United States Patent
Cole et al.

(10) Patent No.: US 9,545,249 B2
(45) Date of Patent: Jan. 17, 2017

(54) OVERTUBE INTRODUCER FOR USE IN ENDOSCOPIC BARIATRIC SURGERY

(71) Applicant: Boston Scientific Scimed, Inc., Maple Grove, MN (US)

(72) Inventors: David Cole, San Mateo, CA (US); Melanie L. Harris, Mountain View, CA (US); Carlos E. Castro, San Jose, CA (US); Jason S. Stewart, Redwood City, CA (US); Samuel T. Crews, Woodside, CA (US); Daniel J. Balbierz, Redwood City, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 279 days.

(21) Appl. No.: 13/964,890

(22) Filed: Aug. 12, 2013

(65) Prior Publication Data
US 2014/0046139 A1    Feb. 13, 2014

Related U.S. Application Data

(63) Continuation of application No. 12/175,274, filed on Jul. 17, 2008, now abandoned.
(Continued)

(51) Int. Cl.
*A61B 17/02* (2006.01)
*A61B 1/00* (2006.01)
(Continued)

(52) U.S. Cl.
CPC ......... *A61B 17/0218* (2013.01); *A61B 1/0051* (2013.01); *A61B 1/00078* (2013.01); *A61B 1/00135* (2013.01); *A61B 1/2736* (2013.01)

(58) Field of Classification Search
CPC ........................... A61B 17/02; A61B 17/0218
(Continued)

(56) References Cited

U.S. PATENT DOCUMENTS

| 1,408,865 A | 3/1922 | Cowell |
| 3,663,965 A | 5/1972 | Lee, Jr. et al. |

(Continued)

FOREIGN PATENT DOCUMENTS

| CH | 680263 A5 | 7/1992 |
| EP | 0 775 471 A1 | 5/1997 |

(Continued)

OTHER PUBLICATIONS

The International Search report and Written Opinion for PCT application PCT/US2008/008726, Oct. 16, 2008, 13 pages (2008).
(Continued)

*Primary Examiner* — Christopher Beccia
(74) *Attorney, Agent, or Firm* — Bookoff McAndrews, PLLC

(57) ABSTRACT

This application describes an overtube device that gives diagnostic and/or therapeutic access to body cavities using natural orifices of the body. The overtube includes an elongate flexible body having a distal portion deflectable in response to activation of a control cable. Proximal features of the overtube include an insufflations port and seals for minimizing loss of insufflations pressure around the shafts of instruments passed through the tube. In some embodiments, retractor elements are including on the distal portion of the overtube.

14 Claims, 17 Drawing Sheets

Related U.S. Application Data

(60) Provisional application No. 60/950,584, filed on Jul. 18, 2007.

(51) Int. Cl.
*A61B 1/005* (2006.01)
*A61B 1/273* (2006.01)

(58) Field of Classification Search
USPC ............... 600/206, 121, 143, 144, 146, 123, 104,600/106, 153
See application file for complete search history.

(56) References Cited

U.S. PATENT DOCUMENTS

| | | | |
|---|---|---|---|
| 4,134,405 A | 1/1979 | Smit | |
| 4,207,890 A | 6/1980 | Mamajek et al. | |
| 4,246,893 A | 1/1981 | Berson | |
| 4,315,509 A | 2/1982 | Smit | |
| 4,331,277 A | 5/1982 | Green | |
| 4,403,604 A | 9/1983 | Wilkinson et al. | |
| 4,416,267 A | 11/1983 | Garren et al. | |
| 4,417,360 A | 11/1983 | Moasser | |
| 4,441,215 A | 4/1984 | Kaster | |
| 4,467,804 A | 8/1984 | Hardy et al. | |
| 4,485,805 A | 12/1984 | Foster, Jr. | |
| 4,501,264 A | 2/1985 | Rockey | |
| 4,607,618 A | 8/1986 | Angelchik | |
| 4,641,653 A | 2/1987 | Rockey | |
| 4,648,383 A | 3/1987 | Angelchik | |
| 4,694,827 A | 9/1987 | Weiner et al. | |
| 4,723,547 A | 2/1988 | Kullas et al. | |
| 4,747,849 A | 5/1988 | Galtier | |
| 4,846,836 A | 7/1989 | Reich | |
| 4,848,367 A | 7/1989 | Avant et al. | |
| 4,899,747 A | 2/1990 | Garren et al. | |
| 4,925,446 A | 5/1990 | Garay et al. | |
| 4,946,440 A | 8/1990 | Hall | |
| 4,969,896 A | 11/1990 | Shors | |
| 4,997,084 A | 3/1991 | Opie et al. | |
| 5,006,106 A | 4/1991 | Angelchik | |
| 5,037,021 A | 8/1991 | Mills et al. | |
| 5,061,275 A | 10/1991 | Wallsten et al. | |
| 5,084,061 A | 1/1992 | Gau et al. | |
| 5,088,979 A | 2/1992 | Filipi et al. | |
| 5,163,952 A | 11/1992 | Froix | |
| 5,211,658 A | 5/1993 | Clouse | |
| 5,234,454 A | 8/1993 | Bangs | |
| 5,246,456 A | 9/1993 | Wilkinson | |
| 5,259,399 A | 11/1993 | Brown | |
| 5,263,629 A | 11/1993 | Trumbull et al. | |
| 5,290,217 A | 3/1994 | Campos | |
| 5,306,300 A | 4/1994 | Berry | |
| 5,314,473 A | 5/1994 | Godin | |
| 5,327,914 A | 7/1994 | Shlain | |
| 5,345,937 A * | 9/1994 | Middleman et al. ......... 600/434 | |
| 5,345,949 A | 9/1994 | Shain | |
| 5,355,897 A | 10/1994 | Pietrafitta et al. | |
| 5,401,241 A | 3/1995 | Delany | |
| 5,403,326 A | 4/1995 | Harrison et al. | |
| 5,405,377 A | 4/1995 | Cragg | |
| 5,431,673 A | 7/1995 | Summers et al. | |
| 5,486,187 A | 1/1996 | Schneck | |
| 5,514,074 A | 5/1996 | Yabe et al. | |
| 5,514,176 A | 5/1996 | Bosley, Jr. | |
| 5,535,935 A | 7/1996 | Vidal et al. | |
| 5,542,949 A | 8/1996 | Yoon | |
| 5,562,239 A | 10/1996 | Boiarski et al. | |
| 5,571,116 A | 11/1996 | Bolanos et al. | |
| 5,577,654 A | 11/1996 | Bishop | |
| 5,593,434 A | 1/1997 | Williams | |
| 5,597,107 A | 1/1997 | Knodel et al. | |
| 5,609,624 A | 3/1997 | Kalis | |
| 5,628,786 A | 5/1997 | Banas et al. | |
| 5,630,539 A | 5/1997 | Plyley et al. | |
| 5,647,526 A | 7/1997 | Green et al. | |
| 5,653,743 A | 8/1997 | Martin | |
| 5,662,713 A | 9/1997 | Andersen et al. | |
| 5,673,841 A | 10/1997 | Schulze et al. | |
| 5,674,241 A | 10/1997 | Bley et al. | |
| 5,706,998 A | 1/1998 | Plyley et al. | |
| 5,709,657 A | 1/1998 | Zimmon | |
| 5,720,776 A | 2/1998 | Chuter et al. | |
| 5,749,918 A | 5/1998 | Hogendijk et al. | |
| 5,762,255 A | 6/1998 | Chrisman et al. | |
| 5,771,903 A | 6/1998 | Jakobsson | |
| 5,792,119 A | 8/1998 | Marx | |
| 5,820,584 A | 10/1998 | Crabb | |
| 5,839,639 A | 11/1998 | Sauer et al. | |
| 5,846,251 A * | 12/1998 | Hart ................ A61B 17/22031 606/127 |
| 5,848,964 A | 12/1998 | Samuels | |
| 5,855,311 A | 1/1999 | Hamblin et al. | |
| 5,855,601 A | 1/1999 | Bessler et al. | |
| 5,856,445 A | 1/1999 | Korsmeyer | |
| 5,861,036 A | 1/1999 | Godin | |
| 5,868,141 A | 2/1999 | Ellias | |
| 5,887,594 A | 3/1999 | LoCicero, III | |
| 5,888,196 A * | 3/1999 | Bonutti ............. A61B 17/0218 600/153 |
| 5,897,562 A | 4/1999 | Bolanos et al. | |
| 5,910,144 A | 6/1999 | Hayashi | |
| 5,922,019 A | 7/1999 | Hankh et al. | |
| 5,947,983 A | 9/1999 | Solar et al. | |
| 5,993,473 A | 11/1999 | Chan et al. | |
| 5,993,483 A | 11/1999 | Gianotti | |
| 6,016,848 A | 1/2000 | Egres, Jr. | |
| 6,051,015 A | 4/2000 | Maahs | |
| 6,086,600 A | 7/2000 | Kortenbach | |
| 6,098,629 A | 8/2000 | Johnson et al. | |
| 6,102,922 A | 8/2000 | Jakobsson et al. | |
| 6,113,609 A | 9/2000 | Adams | |
| 6,120,534 A | 9/2000 | Ruiz | |
| 6,146,416 A | 11/2000 | Andersen et al. | |
| 6,159,146 A | 12/2000 | El Gazayerli | |
| 6,159,238 A | 12/2000 | Killion et al. | |
| 6,197,022 B1 | 3/2001 | Baker | |
| 6,206,930 B1 | 3/2001 | Burg et al. | |
| 6,245,088 B1 | 6/2001 | Lowery | |
| 6,251,132 B1 | 6/2001 | Ravenscroft et al. | |
| 6,254,642 B1 | 7/2001 | Taylor | |
| 6,258,120 B1 | 7/2001 | McKenzie et al. | |
| 6,264,700 B1 | 7/2001 | Kilcoyne et al. | |
| 6,287,334 B1 | 9/2001 | Moll et al. | |
| 6,302,917 B1 | 10/2001 | Dua et al. | |
| 6,358,197 B1 | 3/2002 | Silverman | |
| 6,416,522 B1 | 7/2002 | Strecker | |
| 6,425,916 B1 | 7/2002 | Garrison et al. | |
| 6,454,785 B2 | 9/2002 | De Hoyos Garza | |
| 6,460,543 B1 | 10/2002 | Forsell | |
| 6,461,366 B1 | 10/2002 | Seguin | |
| 6,494,888 B1 | 12/2002 | Laufer et al. | |
| 6,494,895 B2 | 12/2002 | Addis | |
| 6,503,264 B1 | 1/2003 | Birk | |
| 6,506,196 B1 | 1/2003 | Laufer et al. | |
| 6,527,784 B2 | 3/2003 | Adams et al. | |
| 6,540,789 B1 | 4/2003 | Silverman et al. | |
| 6,544,291 B2 | 4/2003 | Taylor | |
| 6,547,801 B1 | 4/2003 | Dargent et al. | |
| 6,558,400 B2 | 5/2003 | Deem et al. | |
| 6,558,429 B2 | 5/2003 | Taylor et al. | |
| 6,572,627 B2 | 6/2003 | Gabbay | |
| 6,572,629 B2 | 6/2003 | Kalloo | |
| 6,575,896 B2 | 6/2003 | Silverman | |
| 6,579,302 B2 * | 6/2003 | Duerig et al. ................ 606/198 |
| 6,592,596 B1 | 7/2003 | Geitz | |
| 6,596,023 B1 | 7/2003 | Nunez et al. | |
| 6,607,555 B2 | 8/2003 | Patterson et al. | |
| 6,627,206 B2 | 9/2003 | Lloyd | |
| 6,632,227 B2 | 10/2003 | Adams | |
| 6,663,639 B1 | 12/2003 | Laufer et al. | |
| 6,675,809 B2 | 1/2004 | Stack et al. | |
| 6,740,098 B2 | 5/2004 | Abrams et al. | |
| 6,740,121 B2 | 5/2004 | Geitz | |

(56) References Cited

U.S. PATENT DOCUMENTS

| | | |
|---|---|---|
| 6,746,460 B2 | 6/2004 | Gannoe et al. |
| 6,755,869 B2 | 6/2004 | Geitz |
| 6,764,518 B2 | 7/2004 | Godin |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,821,285 B2 | 11/2004 | Laufer et al. |
| 6,835,200 B2 | 12/2004 | Laufer et al. |
| 6,845,776 B2 | 1/2005 | Stack et al. |
| 6,916,332 B2 | 7/2005 | Adams |
| 6,932,838 B2 | 8/2005 | Schwartz et al. |
| 6,960,233 B1 | 11/2005 | Berg et al. |
| 6,966,875 B1 | 11/2005 | Longobardi |
| 6,981,978 B2 | 1/2006 | Gannoe |
| 6,981,980 B2 | 1/2006 | Sampson et al. |
| 6,994,715 B2 | 2/2006 | Gannoe et al. |
| 7,011,094 B2 | 3/2006 | Rapackie et al. |
| 7,020,531 B1 | 3/2006 | Colliou et al. |
| 7,025,791 B2 | 4/2006 | Levine et al. |
| 7,033,373 B2 | 4/2006 | de la Torre et al. |
| 7,033,384 B2 | 4/2006 | Gannoe et al. |
| 7,037,344 B2 | 5/2006 | Kagan et al. |
| 7,056,305 B2 | 6/2006 | Garza |
| 7,066,945 B2 | 6/2006 | Hashiba et al. |
| 7,083,629 B2 | 8/2006 | Weller et al. |
| 7,090,699 B2 | 8/2006 | Geitz |
| 7,097,650 B2 | 8/2006 | Weller et al. |
| 7,097,665 B2 | 8/2006 | Stack et al. |
| 7,111,627 B2 | 9/2006 | Stack et al. |
| 7,112,186 B2 | 9/2006 | Shah |
| 7,120,498 B2 | 10/2006 | Imran et al. |
| 7,121,283 B2 | 10/2006 | Stack et al. |
| 7,146,984 B2 | 12/2006 | Stack et al. |
| 7,147,140 B2 | 12/2006 | Wukusick et al. |
| 7,152,607 B2 | 12/2006 | Stack et al. |
| 7,160,312 B2 | 1/2007 | Saadat et al. |
| 7,172,613 B2 | 2/2007 | Wazne |
| 7,175,638 B2 | 2/2007 | Gannoe et al. |
| 7,175,660 B2 | 2/2007 | Cartledge et al. |
| 7,211,114 B2 | 5/2007 | Bessler et |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,229,428 B2 | 6/2007 | Gannoe et al. |
| 7,229,453 B2 | 6/2007 | Anderson et al. |
| 7,255,675 B2 | 8/2007 | Gertner et al. |
| 7,261,722 B2 | 8/2007 | McGuckin, Jr. et al. |
| 7,288,101 B2 | 10/2007 | Deem et al. |
| 7,306,614 B2 | 12/2007 | Weller et al. |
| 7,315,509 B2 | 1/2008 | Jeong et al. |
| 7,316,716 B2 | 1/2008 | Egan |
| 7,320,696 B2 | 1/2008 | Gazi et al. |
| 7,326,207 B2 | 2/2008 | Edwards |
| 7,335,210 B2 | 2/2008 | Smit |
| 7,347,863 B2 | 3/2008 | Rothe et al. |
| 7,347,875 B2 | 3/2008 | Levine et al. |
| 7,354,454 B2 | 4/2008 | Stack et al. |
| 7,399,304 B2 | 7/2008 | Gambale et al. |
| 7,431,725 B2 | 10/2008 | Stack et al. |
| 2001/0011543 A1 | 8/2001 | Forsell |
| 2001/0020189 A1 | 9/2001 | Taylor |
| 2001/0020190 A1 | 9/2001 | Taylor |
| 2001/0021796 A1 | 9/2001 | Silverman et al. |
| 2001/0044595 A1 | 11/2001 | Reydel et al. |
| 2002/0022851 A1 | 2/2002 | Kalloo et al. |
| 2002/0055757 A1 | 5/2002 | Torre et al. |
| 2002/0072761 A1 | 6/2002 | Abrams et al. |
| 2002/0082621 A1 | 6/2002 | Schurr et al. |
| 2002/0099439 A1 | 7/2002 | Schwartz et al. |
| 2002/0161281 A1* | 10/2002 | Jaffe et al. .................. 600/114 |
| 2002/0183767 A1 | 12/2002 | Adams et al. |
| 2002/0183768 A1 | 12/2002 | Deem et al. |
| 2003/0009236 A1 | 1/2003 | Godin |
| 2003/0040804 A1 | 2/2003 | Stack et al. |
| 2003/0040808 A1 | 2/2003 | Stack et al. |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0120289 A1 | 6/2003 | McGuckin, Jr. et al. |
| 2003/0158569 A1 | 8/2003 | Wazne |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208209 A1 | 11/2003 | Gambale et al. |
| 2003/0220660 A1 | 11/2003 | Kortenbach et al. |
| 2004/0006351 A1 | 1/2004 | Gannoe et al. |
| 2004/0024386 A1 | 2/2004 | Deem et al. |
| 2004/0030347 A1 | 2/2004 | Gannoe et al. |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0044364 A1 | 3/2004 | DeVries et al. |
| 2004/0082963 A1 | 4/2004 | Gannoe et al. |
| 2004/0088023 A1 | 5/2004 | Imran et al. |
| 2004/0092892 A1 | 5/2004 | Kagan et al. |
| 2004/0092974 A1 | 5/2004 | Gannoe et al. |
| 2004/0093091 A1 | 5/2004 | Gannoe et al. |
| 2004/0098043 A1 | 5/2004 | Trout, III |
| 2004/0107004 A1 | 6/2004 | Levine et al. |
| 2004/0117031 A1 | 6/2004 | Stack et al. |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158331 A1 | 8/2004 | Stack et al. |
| 2004/0162568 A1 | 8/2004 | Saadat et al. |
| 2004/0172141 A1 | 9/2004 | Stack et al. |
| 2004/0172142 A1 | 9/2004 | Stack et al. |
| 2004/0186502 A1 | 9/2004 | Sampson et al. |
| 2004/0210243 A1 | 10/2004 | Gannoe et al. |
| 2004/0215216 A1 | 10/2004 | Gannoe et al. |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0236419 A1 | 11/2004 | Milo |
| 2004/0243152 A1 | 12/2004 | Taylor et al. |
| 2004/0243223 A1 | 12/2004 | Kraemer et al. |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0033326 A1 | 2/2005 | Briganti et al. |
| 2005/0033345 A1 | 2/2005 | DeLegge |
| 2005/0049718 A1 | 3/2005 | Dann et al. |
| 2005/0065397 A1 | 3/2005 | Saadat et al. |
| 2005/0075654 A1 | 4/2005 | Kelleher |
| 2005/0080444 A1 | 4/2005 | Kraemer et al. |
| 2005/0085787 A1 | 4/2005 | Laufer et al. |
| 2005/0096673 A1 | 5/2005 | Stack et al. |
| 2005/0096750 A1 | 5/2005 | Kagan et al. |
| 2005/0149114 A1 | 7/2005 | Cartledge et al. |
| 2005/0159769 A1 | 7/2005 | Alverdy |
| 2005/0177181 A1 | 8/2005 | Kagan et al. |
| 2005/0183732 A1 | 8/2005 | Edwards |
| 2005/0192599 A1 | 9/2005 | Demarais |
| 2005/0192615 A1 | 9/2005 | Torre et al. |
| 2005/0216040 A1 | 9/2005 | Gertner et al. |
| 2005/0216042 A1 | 9/2005 | Gertner |
| 2005/0240279 A1 | 10/2005 | Kagan et al. |
| 2005/0247320 A1 | 11/2005 | Stack et al. |
| 2005/0250980 A1 | 11/2005 | Swanstrom et al. |
| 2005/0251158 A1 | 11/2005 | Sadat et al. |
| 2005/0251162 A1 | 11/2005 | Rothe et al. |
| 2005/0256533 A1 | 11/2005 | Roth et al. |
| 2005/0256587 A1 | 11/2005 | Egan |
| 2005/0261712 A1 | 11/2005 | Balbierz et al. |
| 2005/0267405 A1 | 12/2005 | Shah |
| 2005/0267499 A1 | 12/2005 | Stack et al. |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0015006 A1 | 1/2006 | Laurence et al. |

(56) References Cited

U.S. PATENT DOCUMENTS

| | | |
|---|---|---|
| 2006/0020278 A1 | 1/2006 | Burnette et al. |
| 2006/0058829 A1 | 3/2006 | Sampson et al. |
| 2006/0106288 A1 | 5/2006 | Roth et al. |
| 2006/0129094 A1 | 6/2006 | Shah |
| 2006/0151568 A1 | 7/2006 | Weller et al. |
| 2006/0155259 A1 | 7/2006 | MacLay |
| 2006/0155311 A1 | 7/2006 | Hashiba et al. |
| 2006/0178560 A1* | 8/2006 | Saadat et al. ............... 600/114 |
| 2006/0178691 A1 | 8/2006 | Binmoeller |
| 2006/0195139 A1 | 8/2006 | Gertner |
| 2006/0253142 A1 | 11/2006 | Bjerken |
| 2006/0271076 A1 | 11/2006 | Weller et al. |
| 2006/0282095 A1 | 12/2006 | Stokes et al. |
| 2006/0287734 A1 | 12/2006 | Stack et al. |
| 2007/0010864 A1 | 1/2007 | Dann et al. |
| 2007/0032800 A1 | 2/2007 | Ortiz et al. |
| 2007/0043384 A1 | 2/2007 | Ortiz et al. |
| 2007/0055292 A1 | 3/2007 | Ortiz et al. |
| 2007/0060932 A1 | 3/2007 | Stack et al. |
| 2007/0073098 A1* | 3/2007 | Lenker et al. ............... 600/30 |
| 2007/0149994 A1 | 6/2007 | Sosnowski et al. |
| 2007/0175488 A1 | 8/2007 | Cox et al. |
| 2007/0191870 A1 | 8/2007 | Baker et al. |
| 2007/0191871 A1 | 8/2007 | Baker et al. |
| 2007/0198074 A1 | 8/2007 | Dann et al. |
| 2007/0219571 A1 | 9/2007 | Balbierz et al. |
| 2007/0239284 A1 | 10/2007 | Skerven et al. |
| 2007/0260327 A1 | 11/2007 | Case et al. |
| 2007/0276432 A1 | 11/2007 | Stack et al. |
| 2008/0033574 A1 | 2/2008 | Bessler et al. |
| 2008/0065122 A1 | 3/2008 | Stack et al. |
| 2008/0116244 A1 | 5/2008 | Rethy et al. |
| 2008/0190989 A1 | 8/2008 | Crews et al. |
| 2008/0195226 A1 | 8/2008 | Williams et al. |
| 2008/0200943 A1* | 8/2008 | Barker ............... A61B 17/3439 606/192 |
| 2008/0208355 A1 | 8/2008 | Stack et al. |
| 2008/0294179 A1 | 11/2008 | Balbierz et al. |
| 2009/0024143 A1 | 1/2009 | Crews et al. |
| 2009/0030284 A1 | 1/2009 | Cole et al. |
| 2009/0125040 A1 | 5/2009 | Hambly et al. |

FOREIGN PATENT DOCUMENTS

| | | |
|---|---|---|
| EP | 1492478 | 1/2005 |
| EP | 1 602 336 A2 | 12/2005 |
| FR | 2768324 A1 | 3/1999 |
| JP | 09-168597 | 6/1997 |
| WO | WO 91/01117 A1 | 2/1991 |
| WO | WO 97/47231 A2 | 12/1997 |
| WO | WO 00/12027 A1 | 3/2000 |
| WO | WO 00/32137 A1 | 6/2000 |
| WO | WO 00/78227 A1 | 12/2000 |
| WO | WO 01/41671 | 6/2001 |
| WO | WO 01/45485 A2 | 6/2001 |
| WO | WO 01/49359 A1 | 7/2001 |
| WO | WO 01/66018 A1 | 9/2001 |
| WO | WO 01/85034 A1 | 11/2001 |
| WO | WO 01/89393 A1 | 11/2001 |
| WO | WO 02/060328 A1 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 A2 | 11/2003 |
| WO | WO 03/094785 | 11/2003 |
| WO | WO 03/099137 A2 | 12/2003 |
| WO | WO 2004/019787 | 3/2004 |
| WO | WO 2004/032760 A2 | 4/2004 |
| WO | WO 2004/037064 | 5/2004 |
| WO | WO 2004/041133 | 5/2004 |
| WO | WO 2004/064680 | 8/2004 |
| WO | WO 2004/064685 | 8/2004 |
| WO | WO 2004/080336 | 9/2004 |
| WO | WO 2004/110285 A1 | 12/2004 |
| WO | WO 2005/037152 A1 | 4/2005 |
| WO | WO 2005/079673 A2 | 9/2005 |
| WO | WO 2005/096991 A1 | 10/2005 |
| WO | WO 2005/105003 | 11/2005 |
| WO | WO 2006/016894 A1 | 2/2006 |
| WO | WO 2006/055365 A2 | 5/2006 |
| WO | WO 2006/127593 | 11/2006 |
| WO | WO 2007/041598 A1 | 4/2007 |
| WO | WO 2008/030403 | 3/2008 |
| WO | WO 2008/033409 | 3/2008 |
| WO | WO 2008/033474 | 3/2008 |
| WO | WO 2008/141288 | 11/2008 |
| WO | WO 2009/011881 | 1/2009 |
| WO | WO 2009/011882 | 1/2009 |

OTHER PUBLICATIONS

Cole et al., Utility U.S. Appl. No. 12/050,169, filed Mar. 18, 2008, U.S. Appl. No. 12/050,169, 85 pages (2008).

Stecco, K. et al., "Trans-Oral Plication Formation and Gastric Implant Placement in a Canine Model", Stecco Group, San Jose and Barosnese, Inc., Redwood City, California (2004).

Stecco, K. et al., "Safety of a Gastric Restrictive Implant in a Canine Model", Stecco Group, San Jose and Barosnese, Inc., Redwood City, California (2004).

U.S. Appl. No. 12/050,169, Cole et al., Not Publsihed.

International Search Report from PCT Patent Application No. PCT/US2002/027177 mailed Feb. 14, 2003.

International Search Report from PCT Patent Application No. PCT/US2003/004378 mailed Aug. 13, 2003.

International Search Report from PCT Patent Application No. PCT/US2003/033605 mailed Mar. 29, 2004.

International Search Report from PCT Patent Application No. PCT/US2003/033606 mailed Mar. 29, 2004.

International Search Report from PCT Patent Application No. PCT/US2003/004449 mailed Aug. 13, 2003.

International Search Report from PCT Patent Application No. PCT/US2004/006695 mailed Sep. 8, 2004.

International Search Report from PCT Patent Application No. PCT/US2004/033007 mailed Feb. 9, 2005.

International Search Report from PCT Patent Application No. PCT/US2005/014372 mailed Jul. 28, 2005.

International Search Report from PCT Patent Application No. PCT/US2006/019727 mailed Apr. 19, 2007.

International Search Report from PCT Patent Application No. PCT/US2006/038684 mailed Feb. 14, 2007.

International Search Report from PCT Patent Application No. PCT/US2007/019227 mailed Feb. 20, 2008.

International Search Report from PCT Patent Application No. PCT/US2007/019833 mailed Feb. 20, 2008.

International Search Report from PCT Patent Application No. PCT/US2007/019940 mailed Mar. 14, 2008.

International Search Report from PCT Patent Application No. PCT/US2008/008729 mailed Aug. 18, 2009.

International Search Report from PCT Patent Application No. PCT/US2008/063440 mailed Aug. 1, 2008.

Felsher, et al., "Mucosal apposition in endoscopic suturing", Gastrointestinal Endoscopy, vol. 58, No. 6, pp. 867-870, (2003).

\* cited by examiner

OVERTUBE INTRODUCER FOR USE IN ENDOSCOPIC BARIATRIC SURGERY

PRIORITY

This is application claims priority to U.S. Provisional Application No. 60/950,584, filed Jul. 8, 2007.

BACKGROUND OF THE INVENTION

This application describes an overtube/introducer device that gives access to body cavities using natural orifices of the body (e.g., esophagus, anus, vagina) for a variety of therapeutic and/or diagnostic procedures. In a particular application, the overtube/introducer enables the introduction of devices into the gastrointestinal tract of a patient via the mouth and esophagus. Therapies to be carried out using the introducer can include procedures designed for the treatment of obesity. The disclosed overtube provides in and out access to the targeted procedural site and protects the body tissue during the procedure from trauma.

The disclosed overtube is suitable for use in an exemplary procedure in which the geometry of the stomach is modified and implantable devices are deployed. The procedure is preferably performed entirely through the naturally existing orifice of the mouth, without additional external incisions.

The exemplary procedure is initiated with the introduction of an overtube into the mouth and, at a minimum, past the pharynx of a patient but preferably reaching and sealing against the lower esophageal sphincter (LES). For reference, FIG. 1 shows the anatomy of the human head and stomach, with reference numerals identifying the following features:
  1. Body of stomach
  2. Fundus
  3. Anterior wall
  4. Greater curvature
  5. Lesser curvature
  6. Lower esophageal sphincter (LES) I gastroesophageal junction
  9. Pyloric sphincter
  10. Pyloric antrum
  11. Pyloric canal
  12. Angular notch
  13. Gastric Canal
  14. Rugal folds The entire exemplary procedure is preferably performed under direct endoscopic visualization, obtained by inserting a flexible endoscope into the overtube prior to its introduction into the patient, though the procedure (or individual steps of the procedure) may also be performed without direct visualization. In cases where an endoscope is used, the endoscope's distal tip may be inserted into a flexible Bougie that incorporates a central lumen allowing direct line-of-sight for the endoscope's illumination and visualization optics. The endoscope with the installed Bougie may then be inserted into the overtube's central lumen until the Bougie protrudes just past the overtube's distal end. This provides a gentle leading edge that facilitates insertion of the Bougie, overtube, and endoscope into the patient's esophagus.

Alternatively the overtube may be inserted over a guide wire; the guidewire inserted under direct visualization using a standard endoscope. A transition member is positioned between the inside diameter of the overtube and the outside diameter of the guidewire providing for a smooth transition. This transition is preferably a long taper, and composed of a soft, flexible material such as silicone.

Once the overtube, endoscope and Bougie have reached the desired position within the esophagus, the endoscope and Bougie are withdrawn from the overtube, and the overtube is left in position. The overtube is now in a position to facilitate the introduction of other tools and devices needed to perform subsequent steps.

With the overtube in the desired position, a special-purpose stapler is inserted which will be used to prepare sites within the stomach wall tissue that will serve as mounting points for implantable devices to be installed in later steps. Staplers suitable for this procedure include those disclosed in the following U.S. applications: U.S. application Ser. No. 11/542,457, filed Oct. 3, 2006, U.S. application Ser. No. 11/900,757, filed Sep. 13, 2007, U.S. application Ser. No. 12/119,329, filed May 12, 2008, U.S. application Ser. No. 12/050,169, filed Mar. 18, 2008.

In one such stapler, the leading distal tip of the stapler mechanism is covered with a compliant, bullet-shaped, Bougie end cap, and incorporates a side-looking window. The smooth Bougie shape of the end cap facilitates introduction of the stapler into the overtube and past the distal end of the overtube into the patient's esophagus or stomach. The side window allows stomach wall tissue to be drawn between the stapler jaws prior to the application of staples. The stapler incorporates a passive flexible length which allows the device to bend freely between the user controls at the proximal end and the stapler mechanism at the distal end. Insertion of the stapler is preferably performed under direct endoscopic visualization, with an endoscope positioned next to the stapler such that its camera optics are located slightly proximal of the stapler's distal end. In this way, the position of the stapler may be visualized at all times, relative to its position within the overtube, esophagus and stomach. However, insertion of the stapler may optionally be performed without using an endoscope for visualization.

With the stapler inserted into the stomach, it may then be positioned relative to the stomach wall near the lower esophageal sphincter as desired. In order to achieve the desired position and visualization, it may be necessary to withdraw or further insert the overtube, or to manipulate certain features of the overtube, in such a way that it advantageously alters the geometry of the tissue and/or the overtube's relative position. When the position of the stapler is judged to be correct, suction is applied to draw stomach wall tissue into the stapler end cap's side-looking window. This positions the stomach wall tissue between the jaws of the stapler, which are then approximated via a physician-controlled actuator to clamp the tissue firmly in position. Once the tissue has been securely fixtured, the suction may be released, as it is no longer needed to retain the stomach tissue. Staples are then deployed by means of a second physician-controlled actuator through the plication, or fold, of stomach tissue between the stapler's jaws to create circular rings about a central point. A hole is created in the plication of stomach tissue at the center of the pattern of stapes simultaneous to the application of the staples. The hole and surrounding circular array of staples create a secure and durable mounting point (e.g., for implantable devices), and will be used in later steps of the procedure. Once the staples have been deployed and the mounting point has been created, the physician releases the plication from the stapler's jaws and any remaining suction. The stapler and endoscope are then withdrawn from the overtube.

For staplers that must be re-loaded prior to the creation of the next mounting point, the stapler is withdrawn from the overtube and the distal stapling mechanism is then reloaded. For self-reloading stapler mechanisms, this step is not required. If reloading is required and has been performed, the reloaded device, Bougie end cap and endoscope are reinserted into the overtube. The process of positioning the stapler mechanism within the stomach described above is repeated so that the next mounting point is identified and created. This process is repeated to produce one or more anchor points, but preferably four mounting points are created. These mounting points may be anywhere within the stomach, but they are preferably located at the 3, 6, 9 and 12 o'clock positions, a fixed distance away from the lower esophageal sphincter. If the mounting points are to be used as anchor points for a flow restrictor of the type used to restrict/obstruct passage of food from the esophagus into the stomach, the preferential distance of the mounting points is such that the position of the exit of a restrictor attached at the mounting points will be immediately adjacent the lower esophageal sphincter. Exemplary restrictor devices include but are not limited to those disclosed in U.S. Pat. Nos. 6,675,809, 6,845,776, 7,097,665, and 7,146,984, U.S. application Ser. No. 10/345,666, filed Jan. 16, 2003, and U.S. application Ser. No. 12/175,242 (abandoned), Endoscopic Implant System and Method, filed Jul. 17, 2008.

Once the desired mounting points have been created with the stapler, the stapler is withdrawn. Next, highly compliant anchors are installed through the hole at the center of each of the mounting points. The anchors have a rivet-like shape with large retaining heads on either end. The anchors are intended to be installed in the holes at the center of the mounting points, remain in position indefinitely or until removed, and be easily removable. The anchors are configured such that they may be grasped and pullet! from one end (herein referred to as the "leading end"), and the resulting tension causes the leading end retaining head to change profile so that it may be drawn through the hole in a mounting point. The other end of the anchor (herein referred to as the "following end") is designed so that tension resulting from drawing it through the mounting hole does not result in a change to its profile, so it cannot be drawn through the mounting hole. Anchors of this type are described in U.S. application Ser. No. 12/175,242 (abandoned), Endoscopic Implant System and Method, filed Jul. 17, 2008.

Anchors are positioned in each of the mounting holes by means of graspers or similar instruments, which pull them, leading end first, through the mounting holes. Once the anchors are installed, the instruments required to insert them are withdrawn from the overtube.

Finally, a restrictor is inserted into the stomach via the overtube. The restrictor is attached to the anchors, and will remain in the stomach after the procedure for an indefinite period of time, such as the point in time when a physician determines the patient has achieved sufficient weight loss. The restrictor is attached to the anchors by drawing the leading end of the anchors through mounting holes in the restrictor using graspers or other instruments, as appropriate.

When the restrictor is attached to the anchors, the procedure is complete and the overtube may be withdrawn from the patient, along with any tools remaining in the lumen it defines (e.g., endoscope, graspers, etc.).

Upon completion of the procedure, the overtube has enabled the deployment of a restrictor, which is attached to anchors that have been implanted into stapled plications in the stomach wall. The passage of food into the stomach from the esophagus has been restricted, altering the patient's feelings of satiety and eating habits.

DETAILED DESCRIPTION

The present invention comprises an overtube intended to be inserted through the mouth into the esophagus of a patient, and extend at least past the pharynx, but preferably far enough for the distal end to seal against the lower esophageal sphincter (LES) at the junction between the stomach and the esophagus. The overtube incorporates features that enable it to facilitate the procedure described in the Background section above though is not restricted to that single procedure. The primary purpose of the present invention is to create and maintain a patent lumen that provides access from the mouth of a patient to the stomach. The outer diameter of the overtube's insertable length allows it to fit within, and be insertable into, a patient's gastrointestinal tract from the mouth to the stomach. The outer surface of the insertable length of the overtube is sufficiently lubricious to allow for its introduction into the esophagus and subsequent manipulations (e.g., further insertion or withdrawal, rotation), and/or is compatible with lubricants commonly used for such procedures. The inner diameter of the overtube's insertable length is sufficiently large to accommodate the insertion of the instruments described in the Background section (e.g., stapler, endoscope, graspers, etc.). Alternatively, the Overtube may be composed of multiple lumens allowing multiple tools to be inserted without interfering with each other. The inner surfaces of the overtube's insertable length are sufficiently lubricious to allow the insertion of instruments and devices, and/or are compatible with lubricants commonly used for such purposes. The overtube conforms to the patient's anatomy and protects anatomical features (e.g. 1 the pharynx, esophagus, lower esophageal sphincter, etc.) from injury that may result from the insertion and manipulation of instruments during the procedure. Further, the overtube provides a means to control the position relative to the LES along the axis of insertion. The position of the distal end of the overtube may be controlled by means of insertion and withdrawal of the instrument (the "Z-level"), by means rotation of (torquing) the insertable length of the overtube, and by optionally incorporating an articulatable, steerable, lockable section somewhere within the insertable length. The overtube assembly may also incorporate expandable elements at or near the distal tip that assist in creating a volume within the stomach, reshaping the walls to facilitate visualization and access. The overtube possesses sufficient tensile, compressive and hoop strength to resist excessive deformation (e.g., extension, compression, collapse, kinking) during use. Materials suitable for short-term mucosal tissue contact are preferable for use in the overtube, e.g., stainless steel, nitinol, silicone, urethanes, PEEK, PVC, etc.

Overview and System Layout

Figure 1:
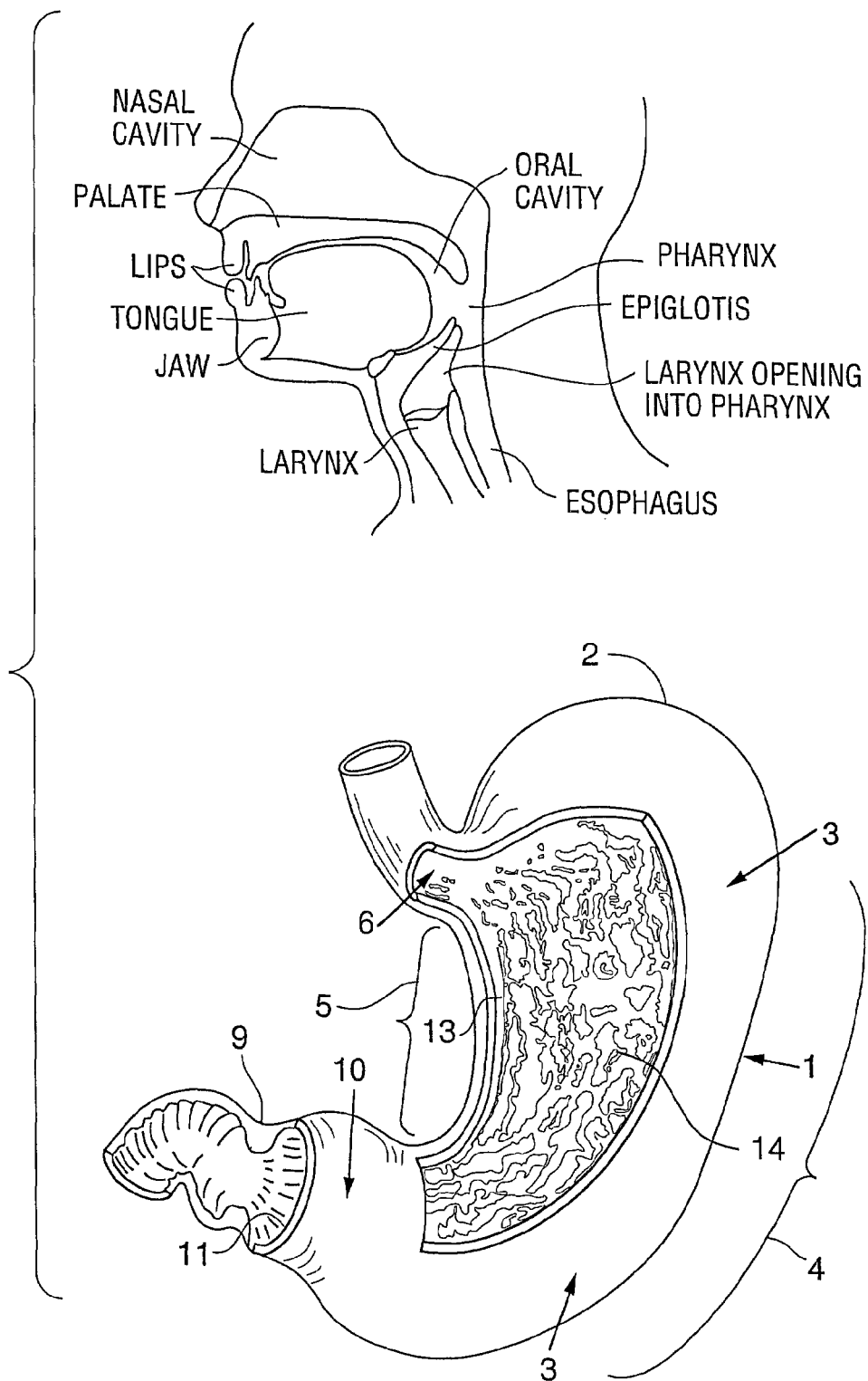
FIG. 1 schematically illustrates certain aspects of the anatomy of the head and stomach.
Figure 2:
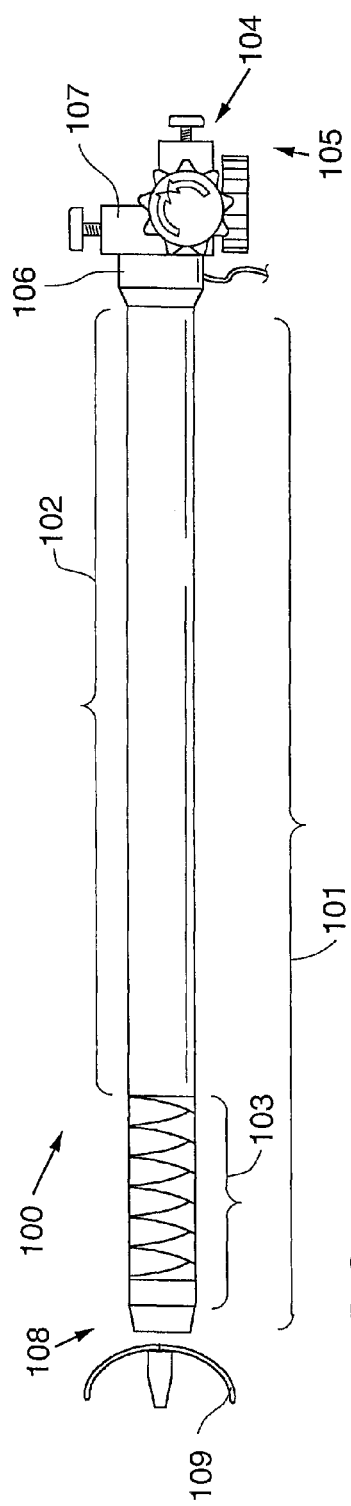
FIG. 2 is a side elevation view of an embodiment of an overtube.

FIG. 2 shows a general system diagram of the overtube 100, and indicates the configuration and names of system components. The insertable length of the overtube 101 is comprised of at least one passive section 102 and optionally at least one articulatable, lockable section 103, which may be steered by means of controls 104 at the proximal end 105 of the assembly. The proximal end also incorporates a terminating end piece 106 and an iron intern ring 107, which serve to support and orient the device during use. At the distal end 108 of the overtube, spreadable fingers 109 may be incorporated to facilitate maneuvers during a procedure. The configuration of the spreadable fingers 109 is determined by controls 104 at the proximal and 105. The construction of the overtube may include some or all of these elements, in different combinations, or it may omit elements, depending on the configuration. This disclosure is intended to include all combinations of inclusion or exclusion of these elements.

Insertion Tube Characteristics

Figure 3:
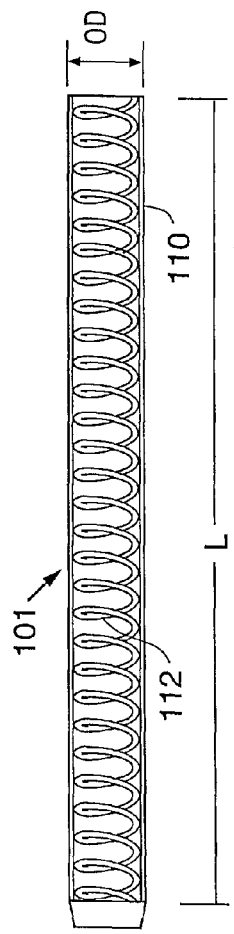
FIG. 3 is a side elevation view of a distal portion of the overtube of FIG. 2.

One embodiment of the present invention's insertable length 101 (FIG. 3) consists of a compliant, flexible, hollow tube. The preferred dimensions of the tube are approximately 38-42 cm (15-16.5 in.) in length (L), with outer diameter (OD) of approximately 1.0-2.0 cm (0.780 in.) (preferably 2.0 cm, but up to approximately 2.2 cm), inner diameter (ID) approximately 1.8 cm (0.700 in.) and wall thickness (T) approximately 0.1-0.2 cm. Larger diameters are preferable when the anatomy will accommodate it, however tubes having smaller dimensions (including those having a diameter proportioned to only accommodate small instruments or endoscopes) are also considered within the scope of this invention. The tube is supported internally at least part of its length by a springform wire 112, intended to support the compliant material comprising the tube 110, and to improve the tube's patency when bent, and to improve the tube's torsional rigidity to facilitate rotating the overtube when in situ during a procedure (its "torquability"). The springform wire reinforcement may extend the full length of the tube, or it may optionally terminate some distance short of the distal or proximal tip. The reinforcement 112 may be encapsulated within the overtube's wall in a thermopolymer or thermoset polymer matrix. The overtube is designed to be compliant and flexible, enabling it to follow the contours and navigate around features of the patient's anatomy, and is capable of conforming to curves with a radius of curvature of at least 1.5 in.

The tube 110 may also incorporate a thin woven mesh, encapsulated within the compliant material as described above, either in conjunction with the springform wire 112 or in lieu of such a wire. The woven mesh may be made of stainless steel, for instance, or aluminum, or any of a variety of polymeric materials. The purpose of embedding mesh within the tube is to substantially increase its torquability while having a minimal effect on its resistance to bending or its minimum radius of curvature.

The outer surface of the insertable length of the overtube should be sufficiently lubricious to allow for its introduction into the esophagus and subsequent manipulations (further insertion or withdrawal, rotation), and/or be compatible with lubricants commonly used in such procedures. The inner surfaces of the overtube's insertable length should also be sufficiently lubricious to accommodate the insertion of instruments and devices, and/or be compatible with lubricants typically used in such applications. In order to achieve sufficient lubricity, inherently lubricious materials may be selected (e.g., PTFE), or coatings may be applied to base materials (e.g., hydrophilic or hydrophobic coatings). Features that prevent locking or binding between components may also be incorporated, such as serrations or surface features similar to those seen on knives designed for slicing meat. Such features facilitate sliding, rather than binding, when elements are moved relative to one another.

Figure 7:
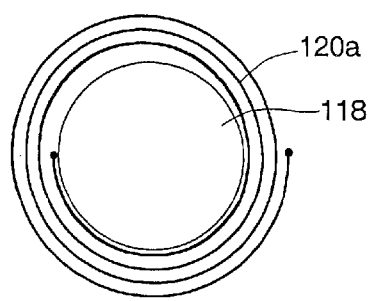
FIG. 7 illustrates an alternate method of making an overtube using a thin sheet of thermopolymer or other suitable material.
Figure 7A:
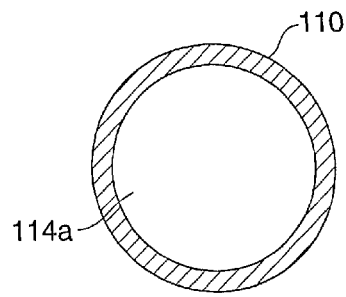
FIGS. 7A-7C are cross-section views illustrating various lumen arrangements for the overtube.
Figure 7B:
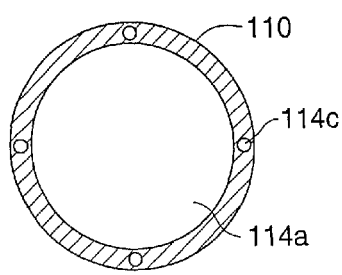
Figure 7C:
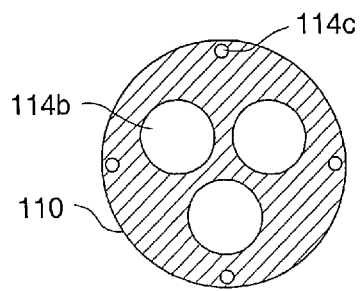

The tube 110 may include a single or large central lumen 114a as shown in FIGS. 7A and 7B, or multiple smaller lumens 114b as in FIG. 7C. Additionally, the tube may incorporate numerous channels 114c completely or partially within the wall. (FIG. 7B). In this way, it comprises a multi-lumen tube, with at least one large central lumen whose primary purpose is facilitating the introduction of instruments and devices to the stomach, and at least one much smaller lumen, through which control cables, fluids, etc. may be routed between the proximal and distal end of the device, or to intermediate points between the ends. In this way, the device presents a single, smooth outer surface to the patient, rather than having any ancillary elements separate from the overtube's insertable section itself in contact with a patient's gastrointestinal tract tissue. This provides protection for the components that may be routed within these lumens, and increases control of cleanliness and thus device function, as well as reduction of requirements for biocompatibility. In some cases, the small channels or lumens 114c within the wall of the overtube may serve more than one purpose: for example, the compressive housing of a Bowden cable may be unnecessary when the control cable is routed within one of the small lumens in the overtube itself, eliminating a component and simplifying the design. For reference, a Bowden cable is comprised of an inner control cable which is housed in an outer housing designed to withstand compressive loads, often a coil tube. Displacements at the proximal end of the inner cable relative to the coil tube housing of a Bowden cable are transmitted to the distal end of the inner cable, and can be used as an actuator to create useful forces and motion relative to the cable housing.

Figure 4A:
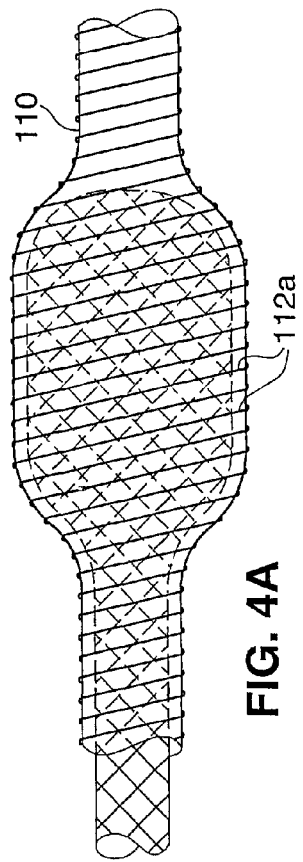
FIG. 4A is a side elevation view of an alternate portion of an overtube, showing expansion of the distal portion in response to introduction of an instrument into the overtube.
Figure 4B:
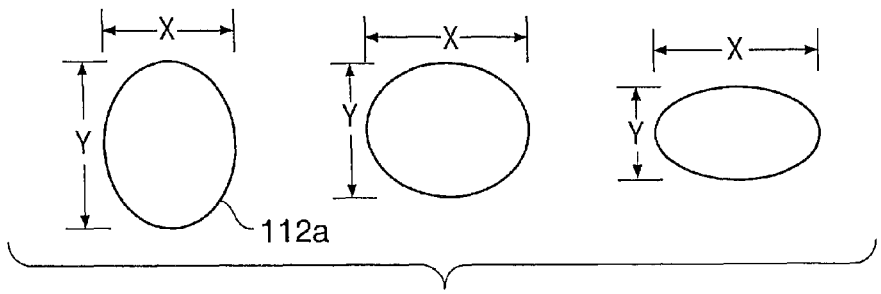
FIG. 4B illustrates a reinforcing ring suitable for use in the deformable overtube of FIG. 4A and shows degrees of deformation of the reinforcement ring in response to instrument advancement through the overtube.
Figure 4C:
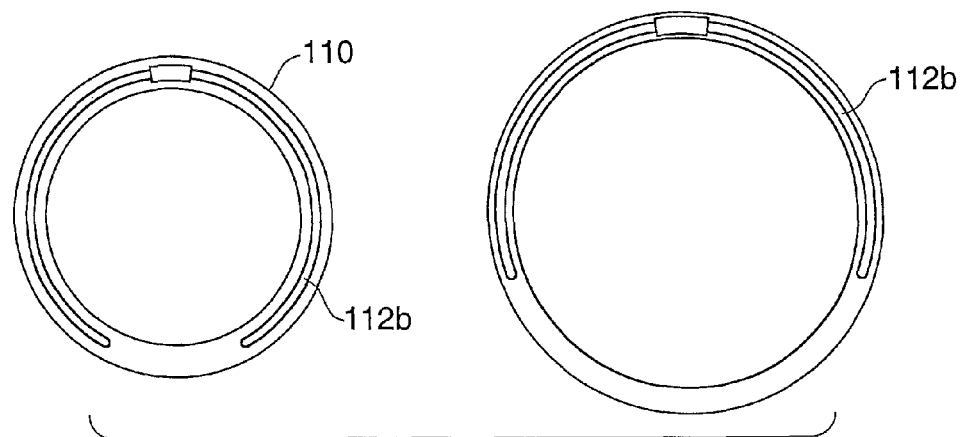
FIG. 4C is a cross-section view of the tube of FIG. 4A, shown as transparent to permit viewing of an alternate reinforcement. The figure shows deformation of the reinforcement ring in response to instrument advancement through the overtube.
Figure 4D:
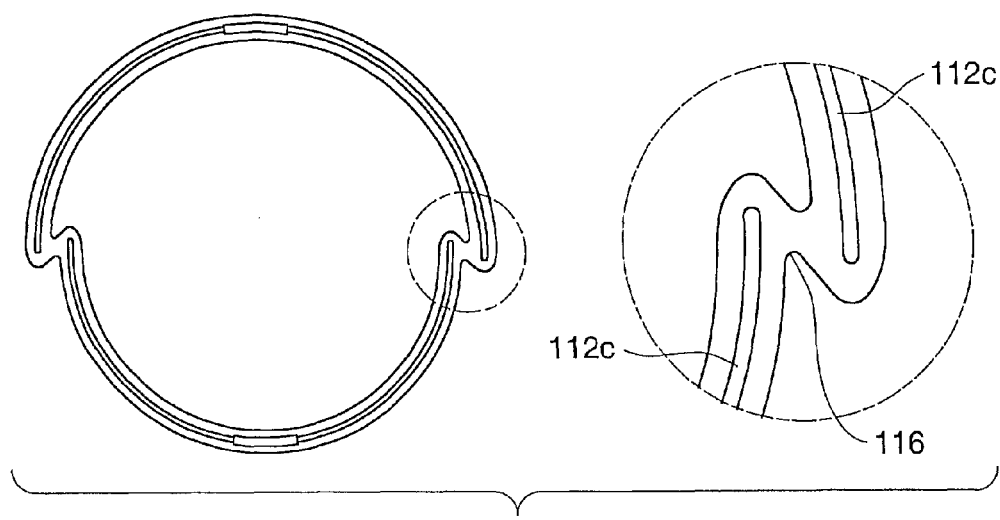
FIG. 4D is similar to FIG. 4C and shows yet another alternate reinforcement.

The construction of the overtube may also be such that it may be expanded as necessary after it has been placed within a patient's anatomy. In the event that large instruments or devices are to be inserted through the overtube into the stomach, it may be beneficial to allow the overtube to expand to accommodate such large components that may otherwise fit too tightly or not at all, and to then return to its unexpanded diameter following passage of the large device. This is illustrated in FIG. 4A. One means of accomplishing this is to form the reinforcing wire rings 112a or coil used to support the overtube structure into elliptical shapes, rather than a circular profile. Such rings could also be encapsulated within a thermopolymer or thermoset polymer matrix, as described above. If the elliptical reinforcing rings are tilted in aspect ratio, as shown in FIG. 4B, the cross sectional shape of the overtube's insertable length is circular under normal circumstances. However, when a large instrument is inserted into the overtube's central lumen to the stomach. the elliptical reinforcing rings comprising the overtube's structural supports can change aspect to present a larger cross sectional area, thus allowing the large instrument to pass through. FIG. 4C shows another embodiment, which relies upon support rings 112b which are not continuous closed forms, but rather are partial rings which have a shape resembling the letter "C". The shape of the partially ring can optionally be in a closed default configuration to resemble the letter "O", with the ends of the ring touching or overlapping, which then dilate and open a gap when expansion forces are applied. Alternatively, more than one wire shape 112c can be combined to create a structure which spans the full circumference of the tube (FIG. 4D). In cases where the ends of the wire endpoints overlap, a fold 116 may be introduced in the thermopolymer or thermoset polymer matrix encapsulating the support to facilitate such dilation (FIG. 4D).

Figure 5A:
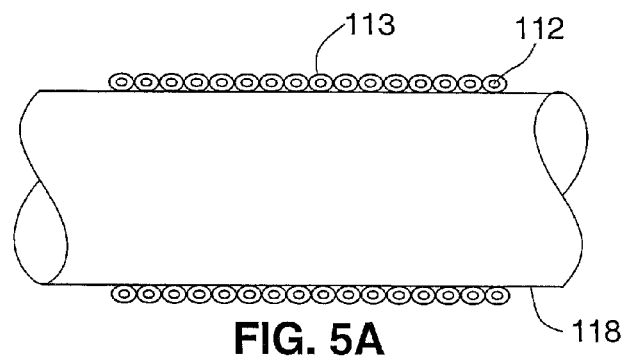
FIG. 5A-5C are a sequence of steps illustrating one embodiment of an overtube manufacturing technique
Figure 5B:
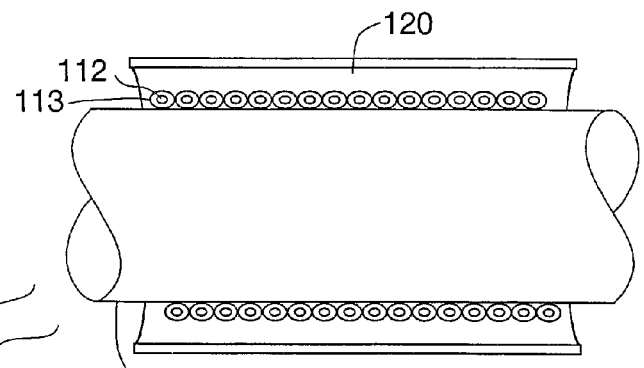
Figure 5C:
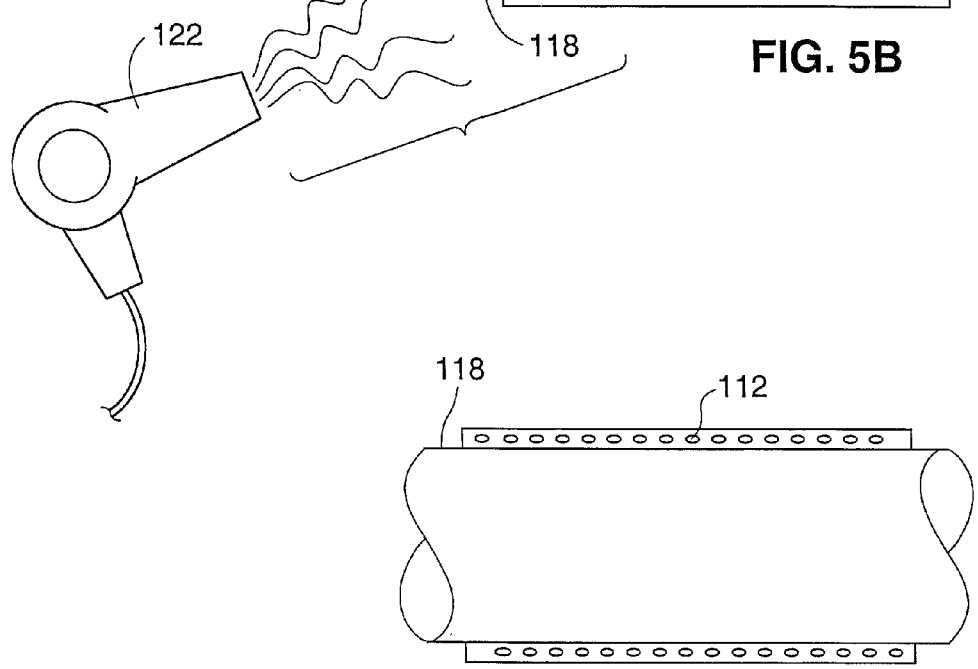
Figure 6A:
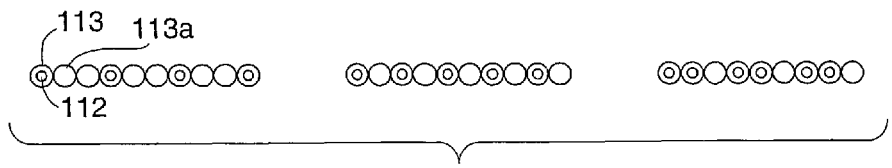
FIG. 6A shows three cross-section views of arrangements of alternating thermoplastic elements with and without wire cores that may be used to form a wall of an overtube in the method of FIGS. 5A-5C.
Figure 6B:
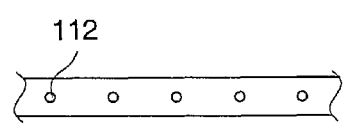
FIG. 6B is a longitudinal cross-section view of one embodiment of an overtube made using thermoplastic and wire core arrangements of the type shown in FIG. 6A.
Figure 6C:
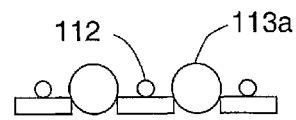
FIGS. 6C and 6D is similar to the drawings of FIG. 6A but shows an alternate arrangement of thermoplastic elements and wire core elements.
Figure 6D:
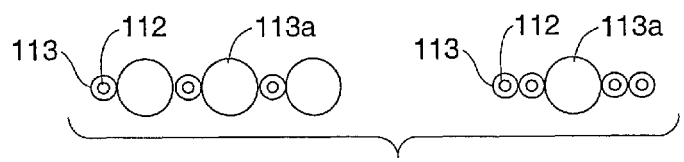

One means of manufacturing the insertable length of the overtube assembly as described (with reinforcing elements encapsulated within a matrix) is to start with a wire 112 which is coated with a thermopolymer 113. This wire may be coiled around a mandrel 118 having the desired outer diameter or profile (the mandrel's outer diameter need not be consistent). This is depicted in FIG. 5A Heat shrink 120 may then be placed over the entire wound wire and mandrel 118 and heat applied, for example with a heat gun 122 or hot box, causing the heat shrink to relax over the wire (FIG. 5B). With the appropriate amount of heat addition, the heat shrink material and any coatings on the wire core will then flow around and encapsulate the wire 112 (FIG. 5C). Once the wire and thermopolymer assembly is complete, the supporting mandrel 118 may be removed, leaving a flexible, hollow tube. The same technique can be performed with a wire mesh in addition to the coil of wire, or instead of the coil of wire. The pitch of the wire wound around the mandrel 118 may also be varied prior to the application of heat shrink. This may be accomplished by alternating thermoplastic elements that have no wire core between windings 113 of those that have the wire core 112, as shown in FIG. 6A. After the application of heat and the flow of the thermopolymer, this results in differences in the space between each turn of wire, affecting the overall pitch (FIG. 6B). The profile of the thermopolymer elements that have no wire core may be round, square, rectangular, or any other desired shape, and the wire 112 need not be originally coated with thermoplastic, nor are they necessarily the same size (FIG. 6C). The cross sectional area of the thermopolymer-only elements need not have the same cross-sectional area as those containing wire (FIG. 6D).

Another means of manufacturing the insertable length of the overtube is to wrap at least one layer of a thin rolled sheet 120a around a mandrel 118, and then fuse the layers together using heat, adhesives or chemical means. This is shown in FIG. 7. Reinforcing elements, e.g., wire and/or mesh, may be incorporated underneath, in between or on top of the rolled sheets in order to create an overtube with encapsulated support elements.

Bougie at Distal End

Figure 8:
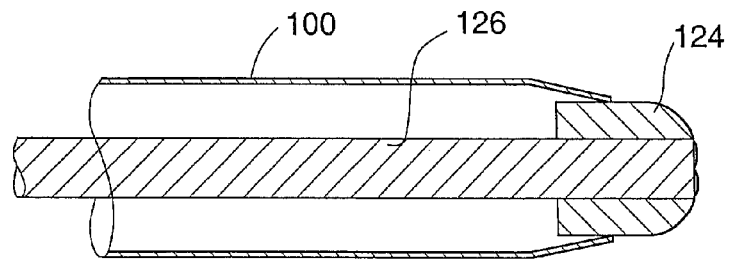
FIG. 8 is a side elevation view of a distal portion of an overtube having a bougie positioned at its distal end.
Figure 8A:
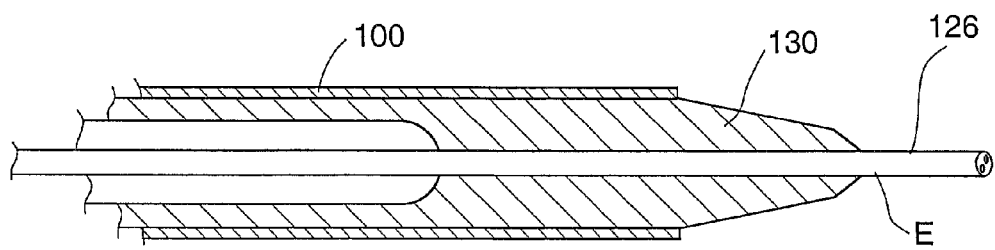
FIG. 8A is a side elevation view of a distal portion of an overtube having a transition member and endoscope extending from its distal end.

The distal tip may maintain the same outer diameter (hereinafter "OD"), inner diameter (hereinafter "ID") and wall thickness as the rest of the tube, or it may taper slightly to form a gentle curve. When an optional taper is incorporated into the distal tip, this serves to facilitate introduction into a patient's gastrointestinal tract, as well as helping to prevent tissue from being drawn into, and potentially pinched between, the overtube and any loose fitting components inserted into its inner lumen. As illustrated in the embodiments of FIGS. 8 and 8A, the distal end of the overtube 100 may be used in combination with a Bougie 124 attached to the distal tip of instruments, such as a flexible endoscope 126 for visualization, inserted to the distal end of the overtube. For reference, a Bougie is a smooth bullet-shaped leading tip that facilitates introduction into a lumen. The Bougie OD should be sized such that it creates a snug fit with the ID of the overtube's distal end.

Figure 8B:
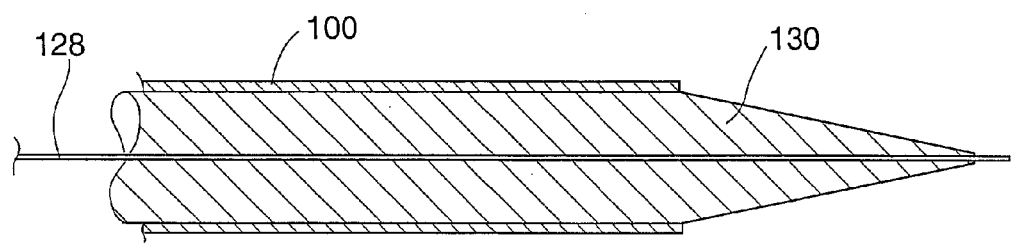
FIG. 8B is a side elevation view of a distal portion of an overtube having a transition member and a guidewire endoscope extending from its distal end.

Alternatively the overtube may be inserted over a guide wire 128 (FIG. 8B); the guidewire inserted under direct visualization using an endoscope. A transition member 130 is positioned between the inside diameter of the overtube and the outside diameter of the guidewire providing for a smooth transition. This transition member preferably includes a long taper, and is composed of a soft, flexible material such as silicone. As shown in FIG. 8A, a similar transition member may be used in place of the Bougie of FIG. 8.

Figure 9A:
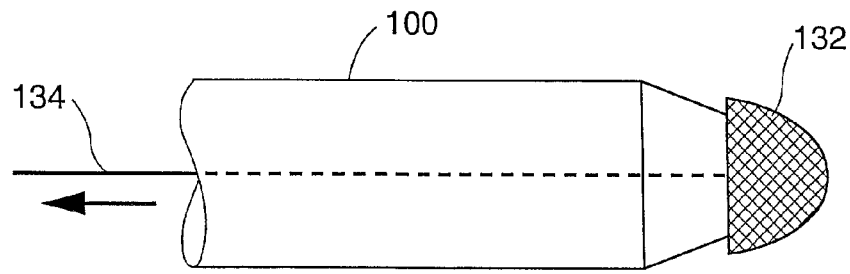
FIG. 9A is a side elevation view of a distal portion of an overtube having an umbrella-shaped leading element.
Figure 9B:
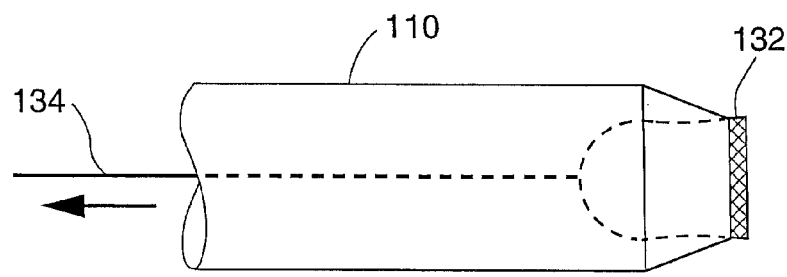
FIG. 9B is similar to FIG. 9A and illustrates inversion of the umbrella element for withdrawal.
Figure 9C:
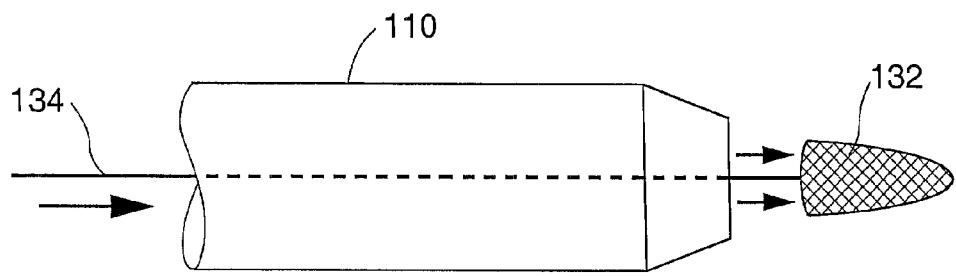
FIG. 9C is similar to FIG. 9A and illustrates advancement and collapse of the umbrella element for withdrawal.

An alternate means of achieving a gently curved leading edge is by means of a protective, thin walled umbrella-like cap 132 positioned at the distal end of the overtube. During insertion, the umbrella is positioned so that it fits snugly over the distal opening of the overtube, maintaining a dome shape and creating the gently curved bullet shape that facilitates insertion and prevents damage to tissue (FIG. 9A). When the desired insertion depth has been achieved with the overtube, the umbrella may be removed by either pulling it back using an element such as a wire 134 or cable and thus inverting it so that it fits into the overtube's lumen (FIG. 9B), or by pushing it forward with an element such as a wire 134 or cable from the distal end of the overtube, causing the umbrella to close before withdrawing it through the overtube (FIG. 9C).

Expandable Elements

Figure 10:
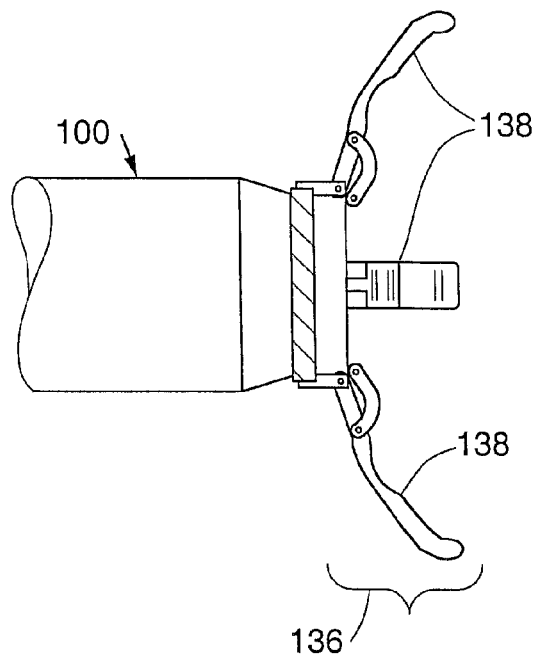
FIG. 10 is a side elevation view of a distal portion of an overtube having spreadable finger elements.

FIG. 10 illustrates how the distal end of the overtube assembly 100 may optionally include attachments or features, such as an array 136 of spreadable fingers 138. Such an expandable element can be used to push the stomach wall away from the overtube, expanding and increasing the amount of space available within the stomach to perform a procedure. An overtube may incorporate or omit such expanders. The benefits of increasing the volume within the stomach include improvements in the ability to introduce and manipulate tools, improvements in the ability to locate plications and staples, improved ability to deploy implantable devices and improved visualization. Essentially, there is more room to work, and this simplifies many of the tasks. In addition to increasing the volume within the stomach, the expanders may be used to reshape the stomach in a way that facilitates the performance of the procedure. For instance, when the expander is at least partially expanded, the overtube may be pulled back slightly to pull up on the LES and reshape the stomach from its normal dome-like shape into something more resembling a cone. During introduction of the overtube into the esophagus, the expander is preferably in its fully retracted state, so that it presents a smooth cone shape that facilitates insertion. Once the desired location has been reached with the distal end of the overtube (e.g., once past the LES), the expander may be caused to open partially or fully to increase the available working volume and reshape the stomach as desired. Expansion of such elements also serves to help position and support the distal end of the overtube relative to the stomach, stabilizing it and helping it maintain position.

Figure 11A:
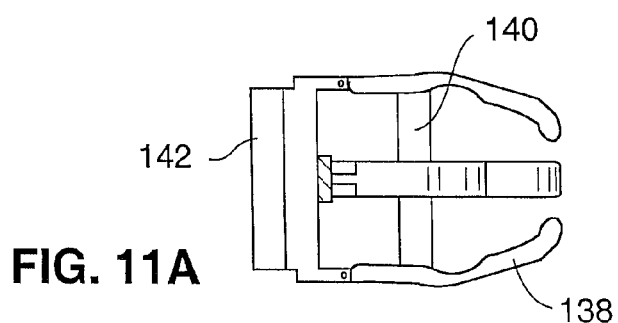
FIG. 11A is a side elevation view of a distal portion of a second embodiment of an overtube having spreadable finger elements, showing the finger elements in the retracted position.
Figure 11B:
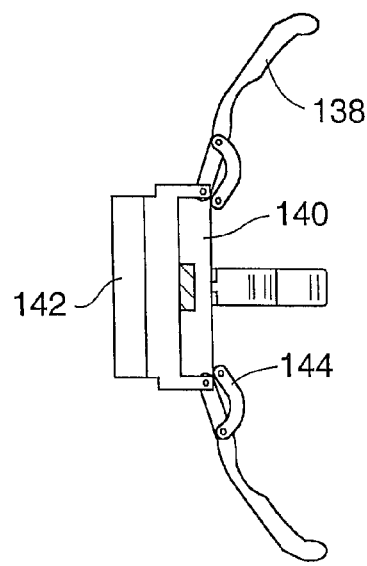
FIG. 11B is similar to FIG. 11A and shows the finger elements in the expanded position.

FIG. 11 shows one embodiment of the expandable elements, in the form of spreadable fingers 138. The position of the fingers may be adjusted and maintained anywhere between a fully closed position (FIG. 11A) and a fully expanded position (FIG. 11B). In this embodiment, this motion is created by changing the relative position of two control rings 140, 142 by means of at least one actuator, for example a Bowden cable. In the illustrated embodiment, movement of ring 140 pivots a hinge 144 coupled to fingers 138. At least part of the more distal control ring 140 may be sized slightly smaller than the more proximal control ring 142 so that it fits or nests at least partially within the proximal control ring 142. During introduction of the overtube into the esophagus, the fingers are preferably in their fully retracted state, so that they present a smooth Bougie-like leading edge that facilitates insertion (FIG. 11A). Once in the desired location, the fingers may be expanded partially or fully to increase the available working volume and reshape the stomach (FIG. 11B). The fingers may be left in this position for the duration of the procedure, or they may be adjusted at any time as desired by the user.

Figure 12A:
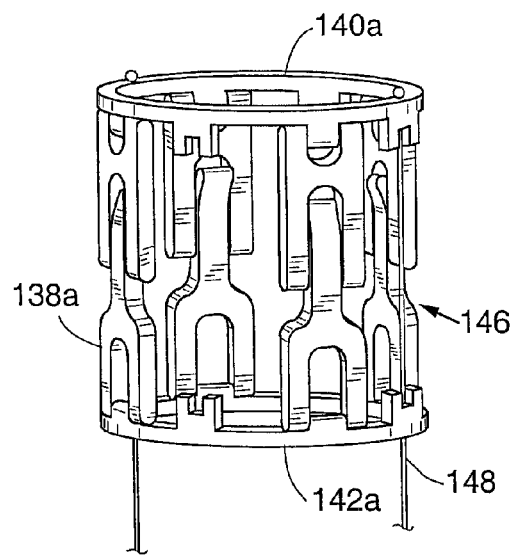
FIG. 12A shows an alternative arrangement of finger elements which may be positioned on the distal end of an overtube as in FIG. 10.
Figure 12B:
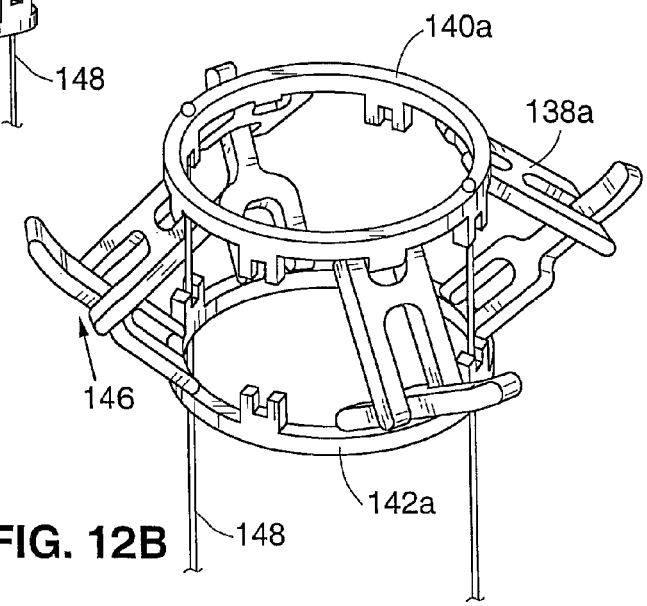
FIG. 12B shows the finger elements of FIG. 12A in a partially expanded position.
Figure 12C:
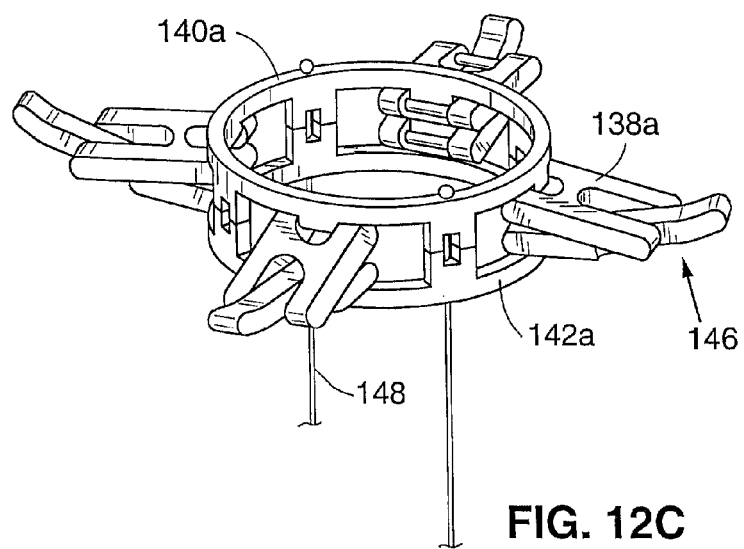
FIG. 12C shows the finger elements of FIG. 12A in the fully expanded position.

An additional embodiment of spreadable fingers is shown in FIG. 12. This version of the expandable element again incorporates two control rings, one distal 140a and one proximal 140b. However, this design differs in that the spreadable fingers do not reach forward (more distal) of the distal control ring when they are fully retracted. Rather, these spreadable fingers include a hinge 146 at or near the midpoint so that they form a link located between the control rings, in effect forming a tube-like, scaffold structure. Like the embodiment described in the previous paragraph and depicted in FIG. 11, pulling the distal control ring 140a towards the proximal control ring 140b causes the fingers to spread and deploy. The rings may be approximated by any number of actuator types, such as the pullwires/Bowden cables 148 depicted in FIG. 12 which can be used to draw the rings 140a, 140b together, such as by drawing the distal ring 140*a* towards the proximal ring 142*a*. At least one Bowden cable may be used, however using two or more Bowden cables allows for balancing the actuation forces more evenly around the control ring. FIG. 12A shows this version of the spreadable fingers in its fully retracted position, FIG. 12B shows it partially expanded, and FIG. 12C shows it fully extended. The control rings may optionally incorporate features that mate when the fingers are fully deployed to provide a positive stop when the full range of motion has been achieved.

Another embodiment of a mechanism that may be used to control the degree of expansion of such spreadable fingers employs a Bowden cable attached at the distal end to each finger in order to determine its position. When tension is applied to each Bowden cable, either separately or simultaneously, the corresponding finger moves radially outward, creating a larger working space.

In cases where an array of spreadable fingers are used to create the expandable element, such as that shown in FIG. 11, these fingers may also be used to maintain orientation during a procedure. Because the image from an endoscope may be rotated and may change unpredictably during the course of a procedure, features that aid in determining location and orientation are helpful. Using landmarks such as the spreadable fingers, especially when they have been individually identified, e.g., with color codes or other markings, aids in determining position of instruments and visualization components. They are especially useful for determining angular position, or "clocking"

Figure 13A:
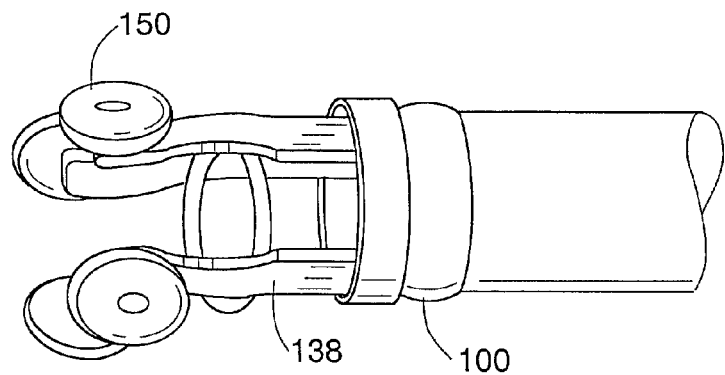
FIGS. 13A and 13B are perspective views of the distal portion of an overtube showing alternative shapes finger elements at the distal end of an overtube.
Figure 13B:
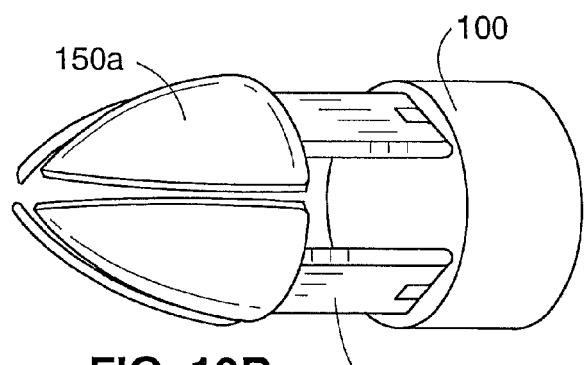
Figure 13C:
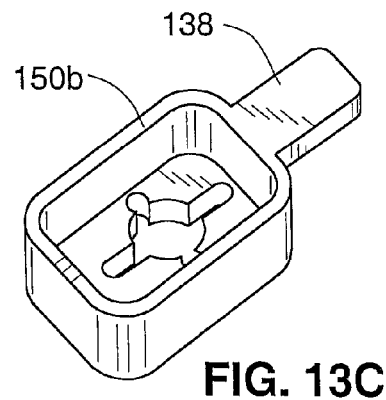
FIG. 13C is a perspective view of a vacuum cup positioned on a finger element.
Figure 13D:
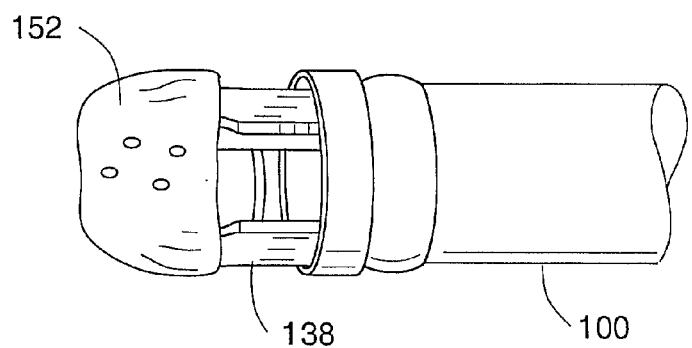
FIG. 13D is a perspective view of a distal portion of an overtube showing an implant device mounted to the finger elements.

In addition to facilitating introduction of the overtube and enabling users to increase the working volume and reshape the stomach during a procedure, the expandable elements, such as the fingers described above and in FIG. 11, may serve as attachment points for a variety of additional devices. In one case, they may have pads 150 attached at their distal ends that increase the surface area they present to the stomach wall when deployed, resulting in a more desirable distribution of forces and a more desirable shape (FIG. 13A). In another case, the pads 150*a* may be shaped to form a cone when the expandable elements are retracted to their closed position, facilitating introduction of the overtube into the patient (FIG. 13B). In another case, the pads may be configured to form suction cups 150*b*, which may be applied to the stomach wall and fixed in place when suction is supplied (FIG. 13C). The use of suction immobilizes the stomach tissue relative to the distal end of the overtube. In another case the pads may have a deployable implant 152, such as the restrictor discussed above, temporarily mounted that, from this lead position at the distal tip of the overtube, may be delivered to one or more desired sites (FIG. 13D). Expansion of the fingers may then be used to deploy the implant within the stomach.

Figure 14:
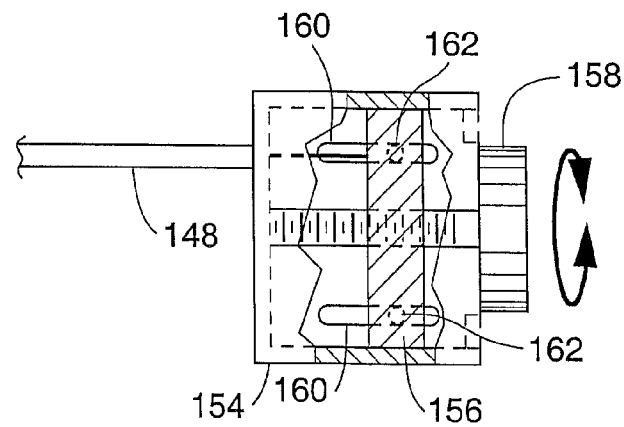
FIG. 14 is a perspective view illustrating a control mechanism for use with expandable members such as the finger elements of FIGS. 10-13D.

One embodiment of a mechanism that may be used to control the degree of spread of such expandable fingers, or any other embodiment that may be effectively controlled by means of Bowden cables 148. is shown in FIG. 14. This control handle serves to adjust the position of an inner control cable relative to an outer compressive housing of a Bowden cable 148. To accomplish this, an outer cup 154 is used in conjunction with a slidable plate 156. The slidable plate 156 is threaded, and acts like a nut when used in combination with a thumbscrew 158, which moves the slidable plate 156 towards or away from the outer cup 154 when it is turned. The thickness of the slidable plate and the clearance between its outer edge and the inside edge of the outer cup serve to keep the slidable plate aligned and prevent it from binding within the cup as it moves. Binding and misalignment may be further prevented via the addition of alignment slots 160, mated to pins 162 that protrude from the slidable plate. The controller may act on at least one Bowden cable, and the cables may be, but are not necessarily, centered or balanced with respect to the slidable plate. Adjustment of the Bowden cable may be accomplished with a barrel adjuster, or similar component. If a barrel adjuster is used, it may be comprised primarily of a screw which has a hole drilled through its central axis. The Bowden cable's compressive housing terminates against the screw head while the inner control cables runs through the screw. When the screw is inserted into a threaded hole, and the cable is attached to a component (such as the slidable plate shown in FIG. 14), the relative positions of the inner cable and outer compressive housing are adjusted.

When retraction of the expandable elements is desired, it may be advantageous or required, depending on the construction, to incorporate components within the mechanism of the expanders to ensure that they reliably retract. For instance, in cases where Bowden cables are used to actuate an expandable element, friction between the control cable and the compressive housing may prevent the expandable element from returning to a retracted position. For the embodiment shown in FIG. 11, this may be accomplished by means of a compression spring that pushes the two control rings apart. Alternately, nitinol spring elements may be incorporated to act upon the outer face of each of the fingers when they are extended, so that they push the fingers back to the retracted position when tension is removed from the Bowden cable that pulls the control rings together.

Figure 15:
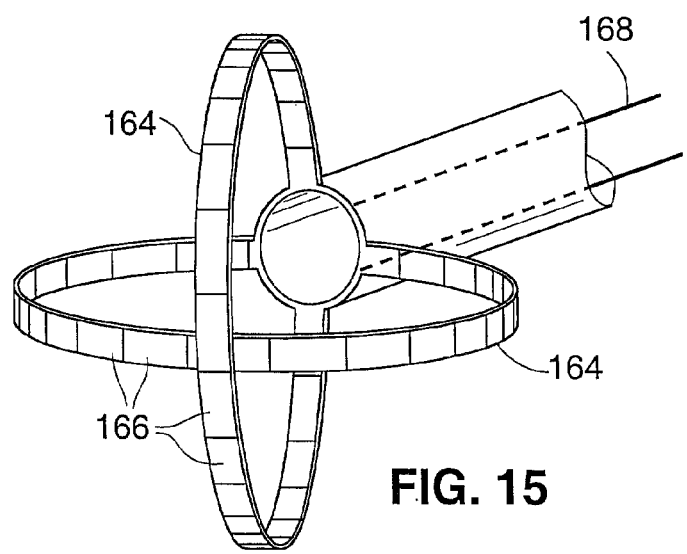
FIG. 15 is a perspective view illustrating a distal portion of an overtube having an alternate arrangement of expandable elements in the form of a pair of expandable hoops.

An alternate embodiment of an expandable element located at the distal end of the overtube or on a separate elongate member passed through the overtube, is shown in FIG. 15. In this embodiment, a fully expanded pair of hoops are comprised of numerous piecewise sections 166 which have central tensioning cables 168 running through their centers. When the tensioning cables are relaxed, the hoop sections are free to move relative to each other, and the result is a flexible chain of short elements. This configuration is well suited for insertion of the device through the overtube. When the tensioning cable is placed in tension, the hoop sections are forced to join together and organize into a shape that creates additional volume within the stomach, such as the hoops, or globe, shape shown. In this example, a hoop shape is depicted, however other shapes are possible and may be desirable, such as triangles, squares, umbrellas, etc.

Articulatable Section

Figure 16:
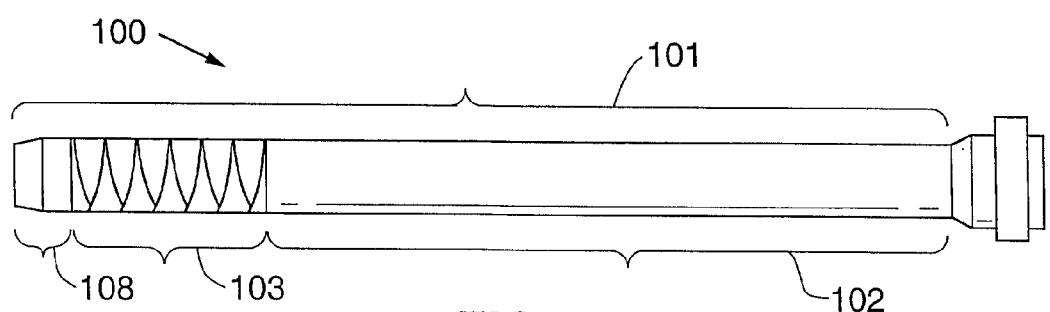
FIG. 16 is a side elevation view of an embodiment of an overtube having an articulating distal portion.

At least one articulatable, lockable section may optionally be incorporated within the insertable length of the overtube. FIG. 16 shows a version of the overtube that incorporates such an articulatable length, labeled 103. The purpose of the articulatable section is to facilitate positional control of instruments and devices inserted through the lumen defined by the overtube. For instance, an articulatable section may be steered (caused to bend at a desirable angle and direction), to impart a "hockey stick" shape to the insertable length of the overtube. Additionally, the shape of the articulatable section may be locked in place by immobilizing or otherwise constraining the actuating elements that determine its shape. The simplest embodiments of the overtube may incorporate no such articulating section, being comprised entirely of a passive tube, as described above and depicted in FIG. 3. However, at least one articulatable section may be incorporated in such a way that it is coaxial and continuous with other passive, non-articulatable sections of the overtube. The articulatable section(s) have an OD, ID and wall thickness similar, but not necessarily equal, to those of the passive overtube sections. FIG. 16 shows the configuration of the articulatable section(s), which may be located at the distal end of the overtube, such that the section 108 has minimal length or zero length. Alternately, the articulatable sections may be located between passive sections of the overtube, such that the length of sections labeled 108 and 102 are non-zero. Similarly, the articulating section may be located at the proximal end of the overtube so that the length of the passive section 102 has minimal or zero length. In cases where more than one articulating section is incorporated, they may be located in any of the positions defined above, and they may be located next to each other or separated by passive sections. The preferred number of articulating sections is either zero or one, and the preferred location of the articulating section is near the distal end of the overtube, such that the length of the passive section 108 is between 0-6 in.

Steering Controls

Figure 22:
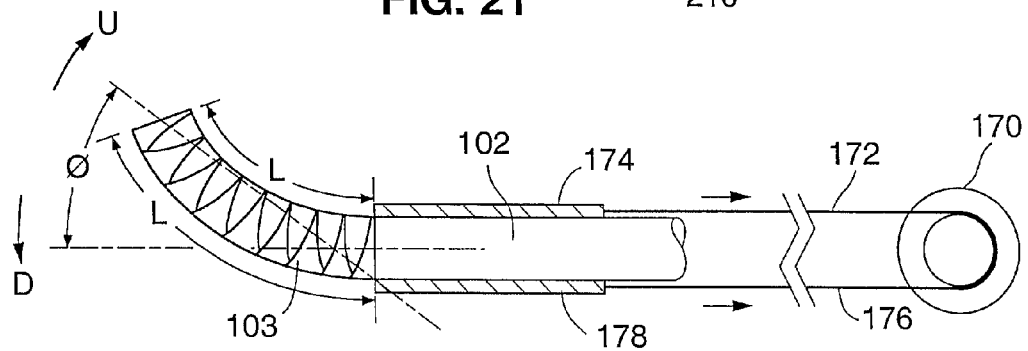
FIG. 22 is a cross-sectional side elevation view showing a distal portion and intermediate portion of an overtube together with proximal control features for use in controlling the articulating section of the overtube.

Steering control of the articulatable section may be achieved by a variety of methods. The preferred method is to control articulation with at least one pull cable, such as a Bowden cable, acting within a coil tube compression housing. A single such control cable can be used to control the shape of the articulatable section in one direction (e.g., to the right), or a single cable can be used in combination with an opposing spring element to cause articulation in two directions (e.g., the spring pulls to the left and the cable pulls to the right). Alternately, two control cables can be used to control articulation in two directions (e.g., left and right). Extending this further, three control cables can be used in combination to allow for articulation in all directions (e.g., left, right, up and down), or four control cables can be used, each directly controlling bending of the articulatable section in each direction. The use of four control cables is the preferred method, as the resulting control is simple and intuitive for the user. The control cables may be used to steer, or determine the curvature of, the articulating section of the overtube. FIG. 22 shows an example where two control cables are used to control the articulation angle 8 of a distal articulatable section in two directions, up (U) and down (D). The coil tube housings associated with the control cables are routed from a rotating control knob 170 located at the proximal end of the overtube assembly, down the length of the overtube to the junction between the length of passive overtube 102 and the articulatable section 103 controlled by the knob 170. Rotating the control knob in one direction results in one control cable being pulled in and an opposing control cable being spooled out. Similarly, rotating the control knob in the opposite direction reverses these motions. The resulting motion and forces are transmitted down the length of the control cables and compression housings to the articulatable length of oveliube, and determine the major (inner) and minor (outer) arc lengths of the articulating section. As an example, FIG. 22 illustrates the case where the control knob is rotated clockwise by the user. This results in the upper control cable 172 being pulled relative to its compression coil tube housing 174, and this defines the minor arc length (l) along the top edge of the articulating length. Simultaneously, the rotation of the knob 170 releases tension on and feeds out the bottom control cable 176 relative to its corresponding compression coil tube housing 178, defining the major arc length (L) along the bottom edge of the articulating section. Variations of this design may incorporate four control cables, each determining the bending of the articulatable section in a different direction, such as left, right, up and down. For this case, two knobs are used. One knob controls one pair of control cables, e.g., the left-right pair, and the other knob controls the other pair of control cables, e.g., the up-down pair. The steering control knobs may optionally be oriented so that their position relates to the direction of steering they control. For example, when two knobs are used with one knob controlling left-right bending and the other knob controlling the up-down bending, the knobs may be rotated relative to one another by 90°. Further, the knobs may be oriented so that the position of the knob controlling bending in the left-right directions is horizontal and the position of the knob controlling bending in the up-down directions is vertical.

Figure 23:
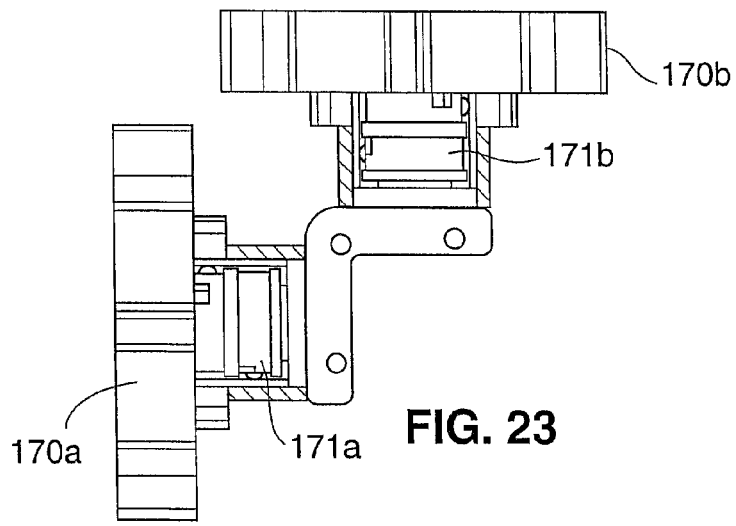
FIG. 23 illustrates articulating control features utilizing separate spools for each pullwire cable.
Figure 24A:
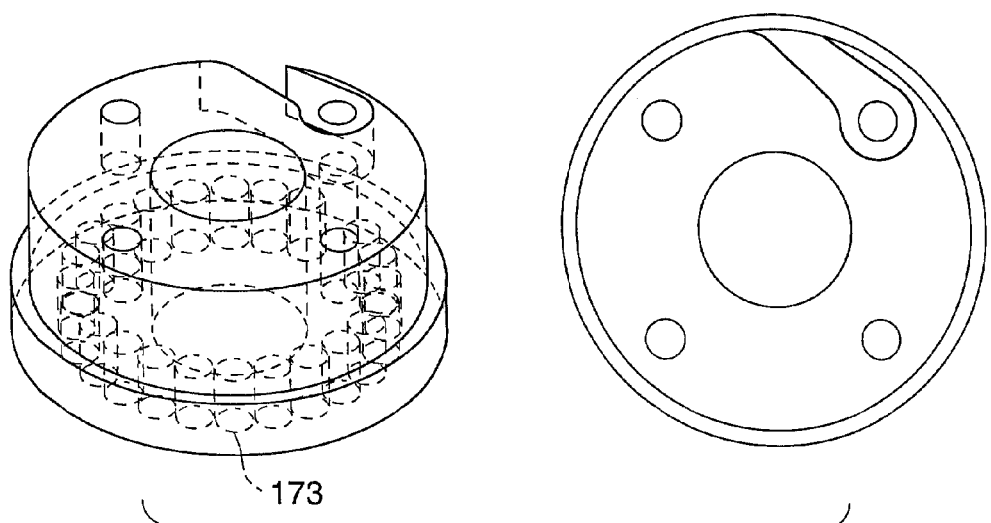
FIG. 24A is a perspective view of a portion of a spool and knob having a selection of cable attachment points allowing for selection and/or adjustment of cable length.
Figure 24B:
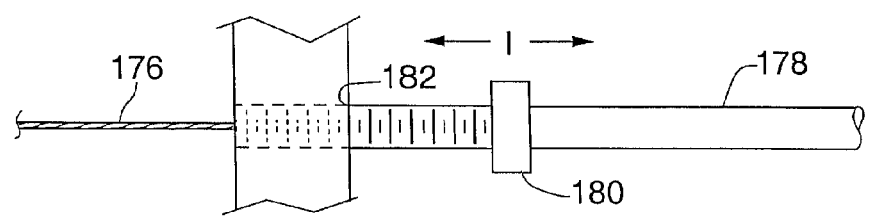
FIG. 24B is a side elevation view showing a barrel adjuster suitable for fine tuning cable length.

The length of each of the Bowden cables is critical to their correct performance, and for this reason elements that facilitate their adjustment are helpful. Even in cases where they have been cut to the exact length required and perfectly installed, cables typically stretch over time and use, and will require periodic adjustment. For this reason, the control knob assemblies may incorporate a number of means of cable adjustment. One useful characteristic of a control knob is to incorporate a means to deal individually with each control cable that terminates there. For instance, if the control knob determines the shape of the articulatable section in the left-right direction, the cable controlling bending to the left can be managed and kept separate and adjusted independently of the cable controlling bending to the right. This may be accomplished by incorporating two completely separate sections 170a, 170b of the control knob, one for each terminating control cable, as illustrated in FIG. 23. In this figure, the 2-part spool is indicated with the reference numerals 171a, 171b. Coarse cable adjustment can be provided by incorporating a multitude of attachment points between the knob described in the paragraph above and the Bowden cable. The spool around which the control cable is wound requires a single potential attachment point, such as a pin, for a control cable, however if multiple potential attachment points are provided, the length of the cable may be adjusted relative to the position of the spool and knob. The example shown in FIG. 24A has potential attachment point 173 spaced every 15°, however this spacing may be any useful interval. The route of the control cable wire to the control knob termination point is preferably but not necessarily smooth, so that it does not present any hard corners or sharp edges to the cable, extending its operating life. Fine cable adjustment may be accomplished with the addition of a barrel adjuster or similar element. In the case of a barrel adjuster, a screw is drilled through its central axis, and the cable's compressive housing terminates against the screw head while the inner control cable runs through the screw. When the screw is inserted into a threaded hole 182, and the cable is attached to a component (such as the spool shown in FIG. 24A), the relative positions of the inner cable and outer compressive housing may be adjusted by the position of the screw. Turning the screw so that it moves towards the cable's termination point (e.g., clockwise for right-handed threads) loosens the cable. Conversely, turning the screw so that it moves away from the cable's termination point (e.g., counter-clockwise for right-handed threads) tightens the cable. This is depicted in FIG. 24B.

Control of an articulating section may also be achieved by means other than Bowden cables. Any appropriate alternate actuation method and energy source may be used, such as hydraulic or pneumatic actuators, which could be used to create the motion and forces needed to bend the articulatable section.

Articulatable Section Construction

Figure 17A:
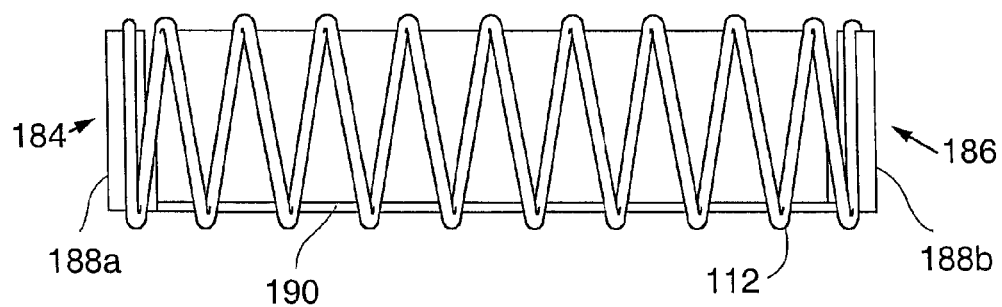
FIG. 17A illustrates an embodiment of a spring assembly suitable for use in the overtube of FIG. 16.
Figure 17B:
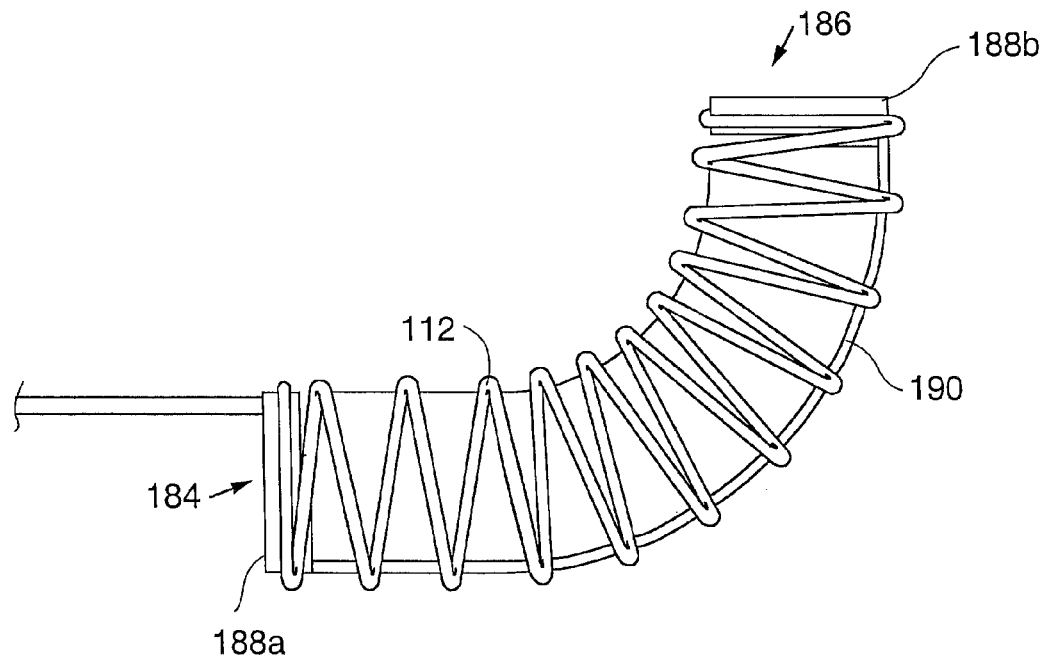
FIG. 17B shows the spring assembly of FIG. 17A in an articulating position.

The articulatable sections may be constructed using a variety of techniques. One simple embodiment consists of a single coil spring element 112 capable of bending as desired, and is shown in FIG. 17A. The proximal 184 and distal 186 ends of the spring are fitted with end caps 188 that provide termination points for actuating elements (described below) and mounting features for attaching them to other parts of the overtube's insertable length. Additional features may be useful for routing components that traverse through the articulatable section, such as Bowden cables running between the user controls at the proximal end and the expandable elements at the distal tip. The spring element 112 may have significant space between the coil windings so that it bends freely when a moment is applied between the distal and proximal ends without changing length significantly. To cause the spring to articulate, a Bowden cable may be used, attached across one side of the outside of the spring element. If the Bowden cable's compressive housing terminates at the proximal end cap 188a of the spring element, and the control cable terminates at the distal end cap 188b of the spring element, pulling on the cable relative to the compressive housing:results in the spring bending in the direction of the cable, as shown in FIG. 17B. A backbone 190 extending through the overtube prevents collapse of the spring during bending. Bending the spring element in other directions is achievable by attaching additional Bowden cables in other locations around the outside of the spring element. A benefit of this construction is that the spring element comprising the articulatable section returns to a straight shape when tension is released from the control cables: its relaxed configuration is straight. The spring element comprising the articulatable section of this construction may be created by attaching a separate spring to passive sections of the overtube to create the full insertable length of the overtube, or it may be formed from the same materials used as the supporting structure of the passive sections of the insertable overtube. This can be accomplished by altering the winding pitch and/or the diameter locally, if needed, where the articulatable section is required.

Figure 18A:
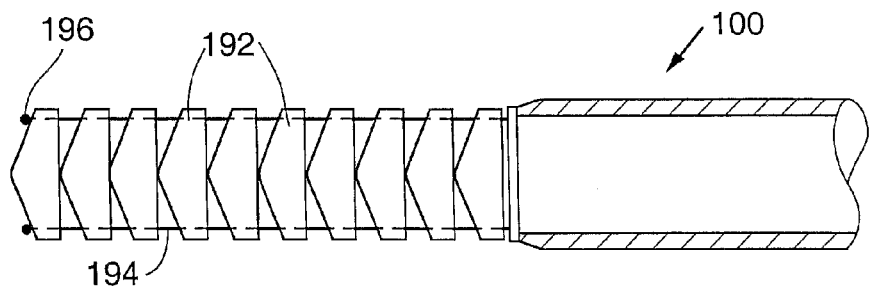
FIG. 18A is a side view of a distal portion of an overtube utilizing a stacked ring construction for the articulating section.
Figure 18B:
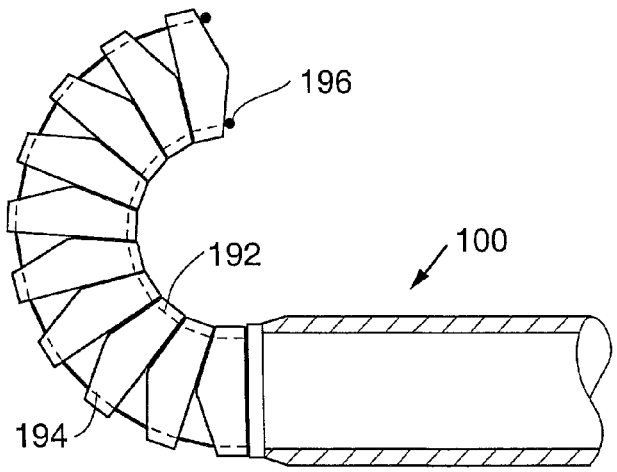
FIG. 18B is similar to FIG. 18A and shows the articulating section in an articulated position.

An alternative means of constructing an articulatable section is to create it by stringing together on cables 194 a succession of rings shaped in such a way that they are allowed to rock relative to one another. The rocking motion can again be controlled through the use of Bowden cables. This construction technique is illustrated in FIG. 18A through D. The shape of each ring is such that it forms an inner lumen, and is preferably (but not necessarily) round. The inner radius r is sized so that it is approximately the same as the inner radius of the rest of the insertable length of the overtube. The outer radius R and the wall thickness T are equal to or as close as possible to the outer radius of the rest of the insertable length of the overtube. Four small through holes are drilled through each ring's wall parallel to the central axis of the overtube, at the 3, 6, 9 and 12 o'clock positions. These holes accept the control cables 194, which run through each ring and hold the assembly together. When viewed from the side, as shown in FIG. 18A, each ring is flat along the bottom surface and has two aligned raised arches along the top surface. In the figure, these are shown in the 12 and 6 o'clock orientation. The raised sections are oriented so that their peaks are coincident with the small holes drilled through the wall. To assemble the articulatable section, a number of rings are strung together using control cables 194. At the distal end of the assembly of rings, each cable is terminated, e.g., with a crimp 196. At the proximal end of the assembly of rings, each compressive housing is terminated. When sufficient tension is applied to a control cable, it will pull back and move into its compressive housing, and the corresponding side of the distal end of the assembly of rings is pulled towards the proximal end. The cables themselves constrain the relative motion of the rings so that the result is piecewise bending. This is shown in FIG. 18B and FIG. 18D. The rings are prevented from sliding relative to each other and losing organization by the cables that connect them. Such rings may be comprised of any of a variety of materials that possess adequate strength, however stainless steel or polycarbonate are preferred.

The arrangement of the rings relative to each other in the assembly determines whether bending in two directions results (e.g., left and right) or whether bending in four directions (e.g., left, right, up and down) is allowed. FIGS. 18A and B show the construction that results in articulation in two directions (left and right). For this construction, the raised portions of each of the rings are all oriented similarly, e.g., from the 12 o'clock position to 6 o'clock position. When control cables are actuated at the 3 o'clock position or the 9 o'clock position, the assembly is caused to rock in the direction of the cable under tension. For this construction, all of the rings contribute to the bending of the assembly. The other two cables (at 12 o'clock and 6 o'clock) are always held at a fixed length and pretension, and applying further tension to them would not result in bending the articulatable section. Instead, these cables serve primarily to string the rings together and stabilize the assembly. They may terminate immediately at the proximal end of the articulatable section, without the use of compressive housings, or they may optionally extend back to the proximal controls.

Figure 18C:
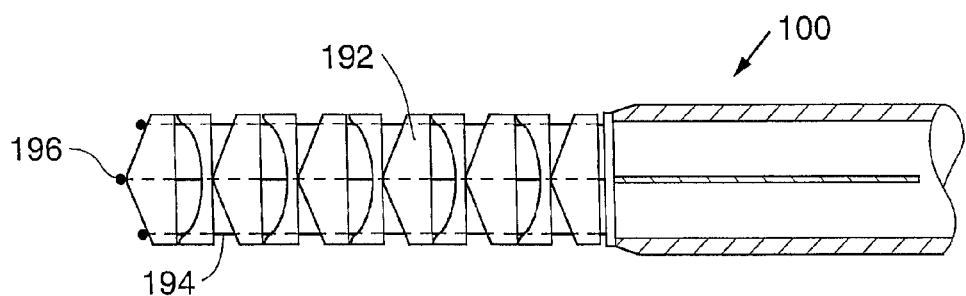
FIGS. 18C and 18D are similar to FIGS. 18A and 18B and show an alternate configuration of stacked ring elements.
Figure 18D:
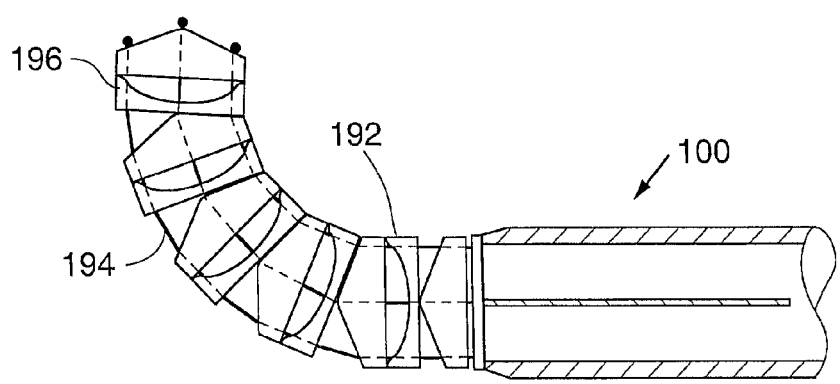

FIGS. 18C and D show a variation of the construction that enables the assembly of rings to articulate in four directions (left, right, up and down). For this construction, the raised portions of each of the rings are alternated, rotated 90° between successive rings. When any of the four control cables is actuated, or combinations of control cables, the assembly is caused to rock in the direction of the cable(s) under tension. For this construction, each ring contributes to the bending of the assembly in two of the four possible directions, such as the left and right pair. Every other ring contributes bending in the left-right directions, alternating with rings that contribute bending in the up-down directions. FIG. 18D illustrates the contributions of each of the rings in the assembly when a single cable is pulled.

These stacked ring embodiments of the articulatable section may also be used to construct unarticulatable sections. Such sections are flexible, but their articulation is not selectable or controllable by a user. When this approach is used, the entire length of the overtube may be constructed using a continuous assembly of rings, oriented in at least one of the ways described above. The shape of at least one region of the assembly may be controllable (e.g., articulatable or steerable) via Bowden cables, as described, while the remaining regions of the assembly which are not controllable have no Bowden cables determining their shape.

Figure 19:
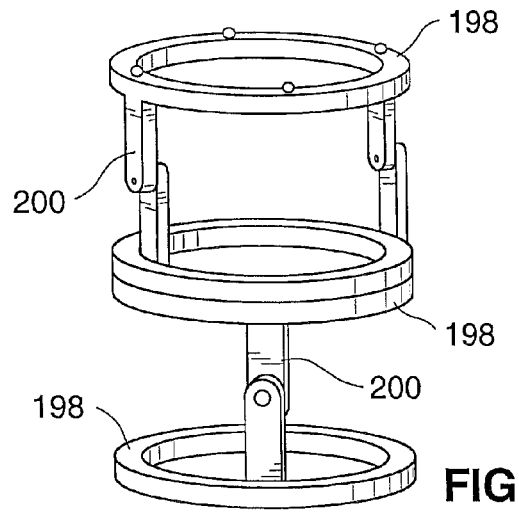
FIG. 19 is a perspective view showing an alternate arrangement of ring elements suitable for use in the articulating section.

Another embodiment of an articulatable section is shown in FIG. 19. In this version, rings 198 that are joined with hinge joints 200 are combined to form an assembly that may be caused to articulate in a desired direction by means of an actuator that pulls differentially in a given direction, such as a Bowden cable. The orientation of successive hinges may alternate in increments of 90° as shown, which enables bending in four directions (e.g., left, right, up and down), or all hinges may be aligned in the same orientation, which will allow for bending in two directions (e.g., left and right). As with the previously described embodiment, the balance of the insertable length of the overtube may also optionally be made using this construction. A single section, multiple sections, or no section may then optionally be made articulatable by means of actuators such as Bowden cables.

Figure 20:
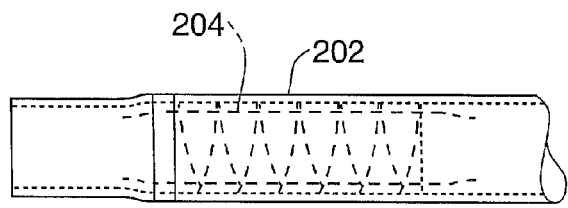
FIG. 20 is a side elevation view of a distal portion of an overtube illustrating optional inner and outer sheaths covering the articulating section.

Regardless of the construction of the articulatable section, it may have either a continuous outer sheath 202 or surface, a continuous inner sheath 04 or surface, or both (e.g., sheaths positioned over the inner and outer surfaces of the articulating rings, coil or other articulating features, or an encapsulation/positioning of such articulating features within the walls of a sheath). This is shown in FIG. 20. The material used to create the sheath preferably offers little resistance to the bending of the articulatable section. For this reason, soft materials, such as a low durometer, thin wall urethane, silicone or similar material are preferred. The overtube's terminating end piece provides an air tight seal against devices inserted through the inner lumen for the purpose of facilitating and maintaining insufflation of the stomach during a procedure, and if the overtube is not a continuously sealed tube along its insertable length, air leaks are likely to occur. Insufflation facilitates visualization and access by increasing the volume of the stomach where the procedure is performed, and when insufflation is not adequate, the procedure may be negatively impacted.

Figure 21:
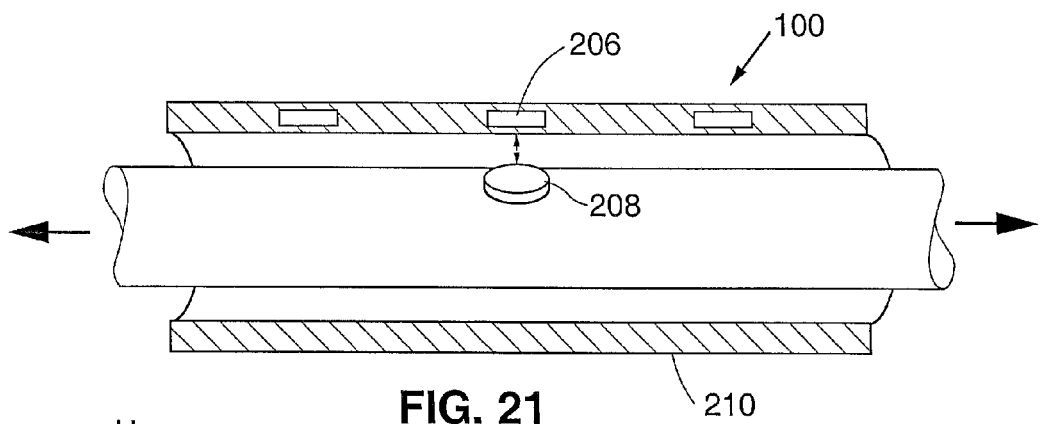
FIG. 21 is a cross-sectional side view of an overtube with an instrument positioned in the lumen of the overtube, and illustrates the use of magnetic indexing.

Components may be added to or incorporated within the overtube to provide tactile feedback to users when instruments within the overtube's ilmer lumen are moved. For example, elements may be used that provide the sensation of indexing, such as a ratcheting feel of engagement and disengagement, when an instrument is inserted into the overtube to specific depth intervals, or rotated relative to the overtube 100 at angular intervals. One embodiment of such a feature makes use of magnetic interactions. If at least one magnet 206 or magnetically attractive element is incorporated into the oveliube, and a corresponding magnet 208 or magnetically attractive element is incorporated into an instrument 210 that moves relative to the overtube, the elements will attract or repel each other as they move into and out of proximity. This is illustrated in FIG. 21. These forces may be useful to the user to indicate that a location of interest has been achieved, or that a certain increment of motion has occurred. Another embodiment of such a feature involves a ball detent, mounted either in the overtube or in an insertable instrument that indexes against indentations in a mating surface. The indentations may be either circular or elongate in shape.

Depth and Angle Markings

Figure 25:
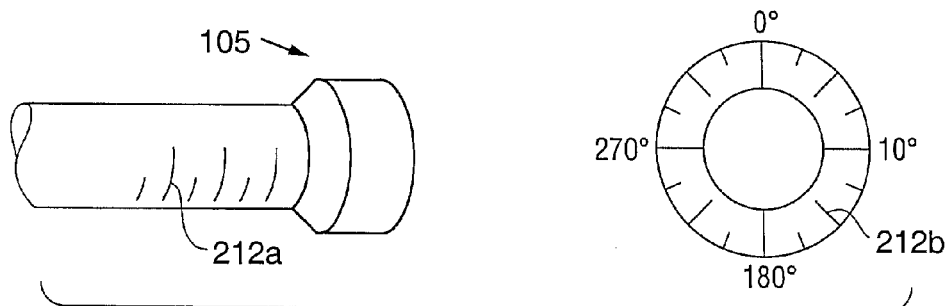
FIG. 25 shows perspective view and proximal end views of an overtube having depth and angle markings

The proximal end of the overtube may incorporate graduated markings indicating depth and radial angle (FIG. 25). The depth markings 212a enable users to quantitatively track and control the depth of insertion of the overtube into the patient, as well as the depth of insertion of instruments, tools and devices into the overtube. The radial angular markings 212b similarly enable users to quantitatively track and control the angular position (also called "clocking") of the overtube and the instruments, tools and devices inserted into the overtube. The depth and angle markings also enable users to repeatedly return an instrument or device to a previously achieved location when required. Additionally, the depth and angle markings enable users to reposition instruments and devices at a known location relative to a previously achieved location. For example, if a physician wishes to create a new stapled mounting point in the stomach wall at a location 90° clockwise and at an equivalent distance from the LES relative to a previously placed stapled mounting. he or she would ensure that the overtube was inserted to the same depth and angular position into the patient for both sequences of operations, that the instruments used were inserted into the overtube at the same depth, and that the instruments were rotated 90° clockwise as indicated on the overtube's angular markings.

Color Coding to Indicate Orientation

Figure 26:
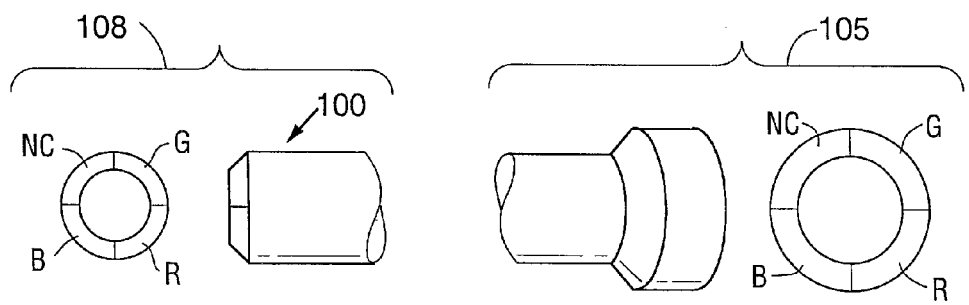
FIG. 26 shows a distal end view, side elevation view, and proximal end view of an overtube and illustrates color coding of angle markings
Figure 27:
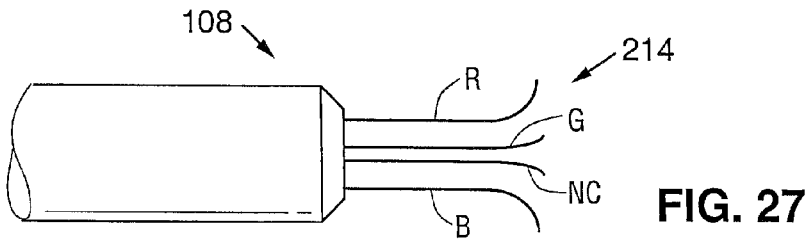
FIG. 27 is a side view of a distal portion of an overtube, illustrating the use of color coded markers positioned within the field of view of an endoscope used in combination with the overtube.

The angular markings at the proximal end of the overtube may be further identified by means of color coding (FIG. 26). For instance, the quadrant from 0° to 90° may be indicated with the color green (G), the quadrant from 90° to 180° with red (R), 180° to 270° with blue (B), and 270° to 0° with no color (NC) added. These color codings may be coordinated with similar markings at the distal end of the overtube 110 which will be visualized with an endoscope. This improves the ability of the user to maintain proper orientation and obtain the desired result when manipulating instruments at the proximal end of the overtube, since it directly corresponds to what he or she observes visually at the distal end of the overtube. The color coding at the distal end of the overtube may be applied anywhere that may be visualized by an endoscope placed inserted through the inner lumen, such as to the overtube itself (including passive and/or articulatable sections), or to components attached to and extending beyond the distal end of the overtube. For instance, expandable elements such as spreadable fingers may be added to the end of the overtube which may each be a unique color. Alternately, components may be extended from the distal end of the overtube for the express purpose of placing color coded markings within the field of view of the endoscope (FIG. 27). These forward-extending components may be of any useful shape, e.g., a tubular antenna, or a garden-hoe-like flag.

The steering controls that determine the angle and direction of the articulatable section may also be marked to correspond to the markings on components at the distal end of the overtube. If, for instance, the spreadable finger located at the top of the overtube (at the 12 o'clock position) is red, the control knob that determines the up-down position of the articulatable section will have a red marking on it indicating which direction it should be turned to cause the articulatable section to bend in the up direction. Similarly, if the spreadable finger located at the bottom of the overtube (at the 6 o'clock position) is blue, then markings on the same knob will incorporate an indication of which direction it should be turned to cause the articulatable section to bend down. This may be done, for example, by marking the knobs with different color arrows.

In addition to indicating which direction to turn each knob to achieve the desired bend angle with the articulatable section, each knob may be marked with an indication of when the articulatable section is approximately straight. A marking indicating the "neutral" position of the articulatable section allows a user to straighten the articulatable section with high confidence, rather than relying on "feel" or for the articulatable section to return to a straight configuration if tension is released on the controlling Bowden cables.

A positive retention force and tactile feedback may also be provided in the steering control knobs by incorporating ball detent components and a sequence of mating indentations. When a user turns a steering control knob, the ball detents can prevent the knob from turning freely, thus preventing the articulatable section from unintentionally returning to its relaxed neutral position. The indexing that occurs as the ball detent moves through the succession of indentations may also provide useful tactile feedback to the user, indicating increments of rotation of a knob and/or certain positions of the articulatable section, such as straight or neutral.

Terminating End Ring

Figure 28:
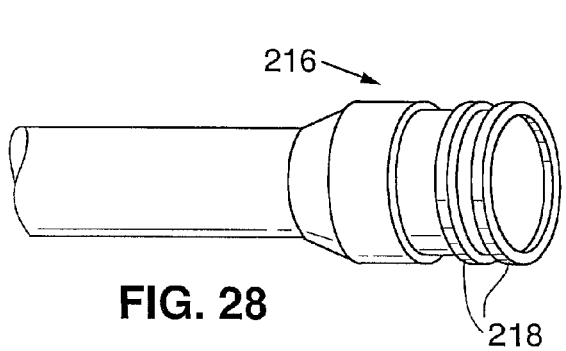
FIG. 28 is a perspective view of a proximal end of an overtube and illustrates a terminating end ring.

The proximal end of the overtube 100 incorporates a terminating end ring 216 (FIG. 28). The end ring 216 is attached to, and is not free to move relative to, the insertable length of the overtube. The end ring 216 incorporates at least one sealing feature 218 for the purpose of creating and maintaining an air-tight seal against components inserted into its inner lumen. When insufflation or suction is applied through the overtube or by instruments passing within the overtube, this seal prevents flow between the inside and the outside of a patient. The sealing feature 218 may take the form of at least one a-ring, but preferably two a-rings. Additionally, the end ring 216 incorporates a port for the introduction of insufflation. This port accepts tubing through which insufflation air may flow. Optionally, a clamp valve may be installed over the insufflation tubing to control the flow of air, or the flow may be controlled by means of turning the insufflation pump on and off.

Fixturing Ring

Figure 29:
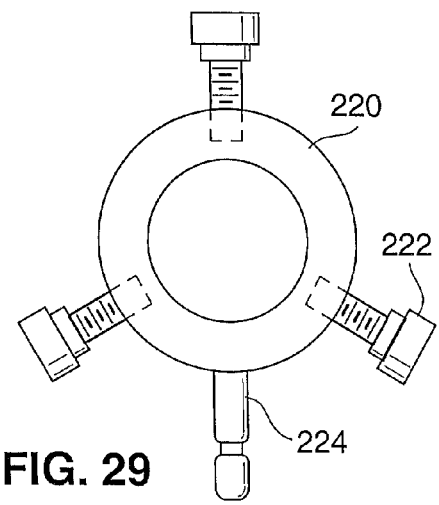
FIG. 29 is a plan view of a proximal end of an overtube and illustrates an iron intern ring.
Figure 30:
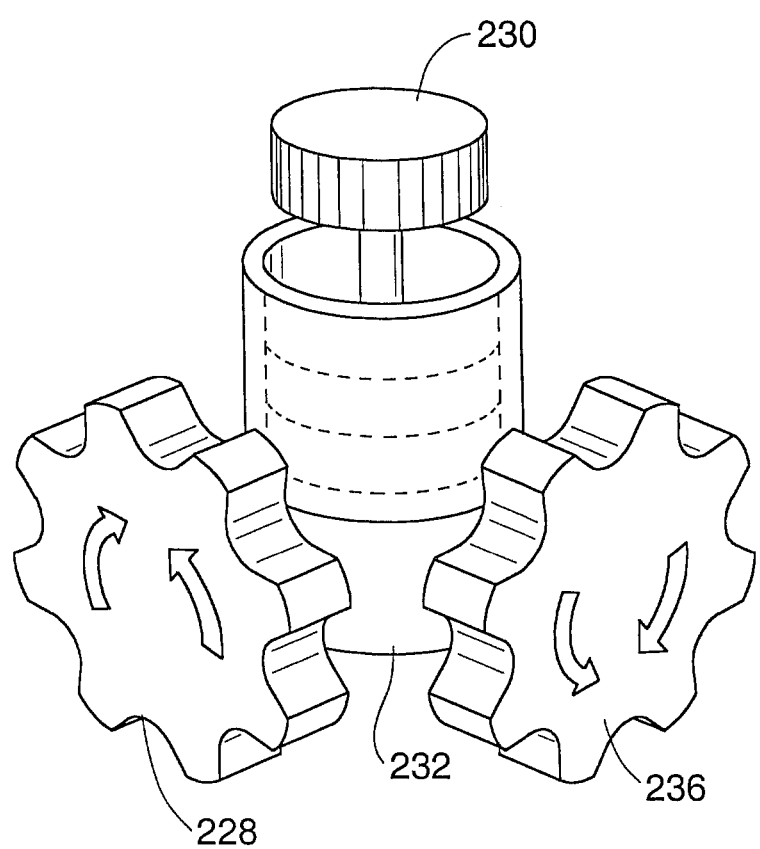
FIG. 30 is a perspective view of a proximal portion of an overtube showing the use of steering controls and expandable element controls on iron an intern ring of the type shown in FIG. 29.

Over the terminating end ring, a fixturing ring 220 (FIG. 29) may be fitted that facilitates attachment to a clamping or fixturing device, such as an iron intern. For this reason, this device may also be referred to as an "iron intern ring". The iron intern ring fits loosely over the terminating end ring, so that it is possible to rotate them relative to each other. The fixturing ring also incorporates at least one tensioning element that, when active, mobilizes the terminating end ring relative to the fixturing ring. This tensioning element may be embodied, for example, by at least one screw 222 that, when tightened, locks the terminating end ring relative to the iron intern ring, preventing rotation and axial motion. Preferably, more than one screw is used to distribute the clamping load. For example, three clamping screws are shown in FIG. 29. This screw may also incorporate features that facilitate frequent adjustment without requiring the use of tools. For instance, large knobs may be located on the screw heads to enable users to tighten and loosen them by hand. The iron intern ring is also the mounting point for elements of the overall device that are inconvenient to rotate in the event that the insertable length of the overtube is torqued. This includes the steering controls for the articulatable, lockable section of the overtube and the position control from the expandable elements, such as the embodiment shown in FIG. 14. In one embodiment, the steering controls (e.g., left-right control 226 and up-down control 228) and the expandable element controller 230 are incorporated into a single component, and this component is attached to the iron intern ring (FIG. 30).

An overtube may be packaged alone or as a system in combination with related components such as staplers and implants of the type referenced in the application, as well as any combination of the following: Bougies, transition members, guidewires, endoscopes etc. The system might further include instructions for use instructing a user to employ the system in accordance with the methods disclosed herein.

As is apparent from the forgoing disclosure, in some embodiments described above, the overtube comprises an articulating section, an actuator for effecting articulation of the articulating section, and an optional locking mechanism allowing the articulating section to be locked in a desired position. In other embodiments described above, the overtube comprises an elongate tube having one or more refraction elements on its distal end, allowing the overtube to create working space within the body (e.g., stomach) while giving access to instruments passed through its lumen.

It should be recognized that a number of variations of the above-identified embodiments will be obvious to one of ordinary skill in the art in view of the foregoing description. Accordingly, the invention is not to be limited by those specific embodiments and methods of the present invention shown and described herein. The applications and methods listed are not limited to the treatment of diseases or procedures listed. Modifications of the above described methods and tools and variations of this invention that are obvious to those of skill in the art are intended to be within the scope of this disclosure. Moreover, the disclosed embodiments may be combined with one another in varying ways to produce additional embodiments.

Any and all patents, patent applications and printed publications referred to above, including those relied upon for purposes of priority, are incorporated herein by reference.

The invention claimed is:

1. An endogastric overtube, comprising:
a flexible elongate tube extending along a longitudinal axis;
at least one lumen extending along a length of the elongate tube; and
a retractor assembly proximate a distal end of the elongate tube, the retractor assembly including:
a plurality of control elements extending disposed about the longitudinal axis, the plurality of control elements including at least a first control element and a second control element; and
a plurality of expandable elements coupled to the plurality of control elements, each expandable element of the plurality of expandable elements being configured to deflect at a hinge and transform from a retracted configuration to an expanded configuration in response to a change in position of at least one control element of the plurality of control elements,
wherein each expandable element includes a first end and a second end, and for each expandable element, the first end is coupled to the first control element, and a connection location between the first end and the second end is coupled to the second control element through the hinge, such that in the expanded configuration, the second end is positioned radially outwards of the first end.

2. The endogastric overtube of claim 1, wherein each expandable element is configured to transform from the retracted configuration to the expanded configuration when a distance between the first and second control elements of the plurality of control elements decreases, and transform from the expanded configuration to the retracted configuration when the distance increases.

3. The endogastric overtube of claim 1, wherein the second control element is positioned distal to the first control element, and wherein the first and second control elements extend circumferentially around the longitudinal axis, and a first expandable element of the plurality of expandable elements extends along the longitudinal axis from a first end coupled to the first control element to a second end distal to the first end.

4. The endogastric overtube of claim 1, wherein an external diameter of the second control element is smaller than an internal diameter of the first control element such that, in a fully expanded configuration of the plurality of expandable elements, the second control element nests at least partially within the first control element.

5. The endogastric overtube of claim 1, wherein in both the expanded configuration and the retracted configuration, a length of a first expandable element of the plurality of expandable elements between the connection location and the second end extends distal to the second control element.

6. The endogastric overtube of claim 1, wherein the first control element and the second control element includes mating features that contact each other in a fully expanded configuration of the plurality of expandable elements.

7. An endogastric overtube, comprising:
- a flexible elongate tube extending longitudinally between a proximal end and a distal end;
- at least one lumen extending between the proximal end and the distal end;
- a first control element positioned proximate the distal end of the elongate tube;
- a second control element positioned distal to the first control element; and
- a plurality of expandable elements pivotably coupled to the first control element and the second control element, the plurality of expandable elements being configured to deflect at a hinge and transform from a retracted configuration to an expanded configuration when the second control element is moved towards the first control element,
- wherein each expandable element includes a first end and a second end, and for each expandable element, the first end is coupled to the first control element, and a connection location between the first end and the second end is coupled to the second control element through the hinge, such that in the expanded configuration, the second end is positioned radially outwards of the first end.

8. The endogastric overtube of claim 7, wherein a first expandable element of the plurality of expandable elements extends longitudinally from the first end to the second end.

9. The endogastric overtube of claim 8, wherein in both the expanded configuration and the retracted configuration, a length of the first expandable element between the connection location and the second end extends distal to the second control element.

10. The endogastric overtube of claim 8, wherein an external diameter of the second control element is smaller than an internal diameter of the first control element such that, in a fully expanded configuration of the plurality of expandable elements, the second control element nests at least partially within the first control element.

11. The endogastric overtube of claim 7, wherein each of the first control element and the second control element includes mating features that contact each other in a fully expanded configuration of the plurality of expandable elements.

12. An endogastric overtube, comprising:
- a flexible elongate tube extending along a longitudinal axis between a proximal end and a distal end; and
- a retractor assembly, the retractor assembly including:
  - a first control ring disposed about the longitudinal axis and positioned proximate the distal end of the elongate tube;
  - a second control ring disposed about the longitudinal axis and positioned distal to the first control ring; and
  - a plurality of expandable elements extending longitudinally from a first end to a second end, wherein each expandable element of the plurality of expandable elements includes a hinge, and is configured to:
    - transform from a retracted configuration to an expanded configuration when a longitudinal distance between the first control ring and the second control ring is decreased; and
    - transform from the expanded configuration to the retracted configuration when the longitudinal distance is increased,
  - wherein an external diameter of the second control ring is smaller than an internal diameter of the first control ring such that, in a fully expanded configuration of the plurality of expandable elements, the second control ring nests at least partially within the first control ring.

13. The endogastric overtube of claim 12, wherein, for each expandable element, the first end is coupled to the first control ring and a connection location between the first end and the second end is coupled to the second control ring, such that in the expanded configuration, the second end is positioned radially outwards of the first end.

14. The endogastric overtube of claim 13, wherein an external diameter of the second control ring is smaller than an internal diameter of the first control ring such that, in a fully expanded configuration of the plurality of expandable elements, the second control ring nests at least partially within the first control ring.

* * * * *